US011911517B2

(12) United States Patent
Zumeta Perez et al.

(10) Patent No.: US 11,911,517 B2
(45) Date of Patent: Feb. 27, 2024

(54) HIGH CONCENTRATION SUSPENSION FORMULATION FOR COLD AND FLU SOFT GEL CAPSULE MEDICATIONS

(71) Applicant: BAYER HEALTHCARE LLC, Whippany, NJ (US)

(72) Inventors: Javier Zumeta Perez, Alcala de Henares (ES); Blanca Alvarez Maluenda, Madrid (ES); Maria Pilar Sanz Saiz, Madrid (ES); Maria Elena Iglesias Piñeiro, Madrid (ES); Anthony Bell, Andover, NJ (US); Reinhard Walter, Morristown, NJ (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 16/410,599

(22) Filed: May 13, 2019

(65) Prior Publication Data

US 2019/0350865 A1 Nov. 21, 2019

Related U.S. Application Data

(60) Provisional application No. 62/816,727, filed on Mar. 11, 2019, provisional application No. 62/672,457, filed on May 16, 2018.

(51) Int. Cl.
*A61K 9/48* (2006.01)
*A61K 31/09* (2006.01)
*A61K 31/137* (2006.01)
*A61K 31/167* (2006.01)
*A61K 31/4402* (2006.01)
*A61K 31/485* (2006.01)

(52) U.S. Cl.
CPC .......... *A61K 9/4825* (2013.01); *A61K 9/4866* (2013.01); *A61K 9/4883* (2013.01); *A61K 31/09* (2013.01); *A61K 31/137* (2013.01); *A61K 31/167* (2013.01); *A61K 31/4402* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 4,115,315 A * | 9/1978 | Marinelli | A61K 9/50 264/4.3 |
| 4,780,316 A * | 10/1988 | Brox | A61K 9/4858 424/456 |
| 5,360,615 A | 11/1994 | Yu et al. | |
| 5,505,961 A | 4/1996 | Shelley et al. | |
| 5,510,389 A | 4/1996 | Dhabhar | |
| 5,759,579 A | 6/1998 | Singh et al. | |
| 6,217,902 B1 * | 4/2001 | Tanner | A61K 9/4833 424/456 |
| 6,221,391 B1 | 4/2001 | Rouffer | |
| 6,287,985 B1 | 9/2001 | Heffner et al. | |
| 6,294,192 B1 | 9/2001 | Patel et al. | |
| 6,383,471 B1 | 5/2002 | Chen et al. | |
| 6,387,400 B1 | 5/2002 | Tindal et al. | |
| 6,846,495 B2 | 1/2005 | Dobrozsi et al. | |
| 6,992,218 B2 | 1/2006 | Dietlin et al. | |
| 7,029,698 B2 | 4/2006 | Waranis et al. | |
| 8,518,439 B2 | 8/2013 | Puttachari et al. | |
| 9,480,667 B2 | 11/2016 | Lopez et al. | |
| 9,504,656 B2 | 11/2016 | Vamvakas et al. | |
| 9,867,779 B2 | 1/2018 | Zhao et al. | |
| 10,022,339 B2 | 7/2018 | Martin et al. | |
| 2004/0157928 A1 | 8/2004 | Kim et al. | |
| 2005/0249802 A1 | 11/2005 | Khanolkar et al. | |
| 2011/0020440 A1 | 1/2011 | Modi et al. | |
| 2012/0301544 A1 | 11/2012 | Okutan et al. | |
| 2014/0094438 A1 | 4/2014 | Mitchell | |
| 2017/0095736 A1 | 4/2017 | Giro et al. | |
| 2017/0100391 A1 | 4/2017 | Martin et al. | |
| 2017/0319479 A1 | 11/2017 | Agisim et al. | |
| 2018/0049979 A1 | 2/2018 | Zhao et al. | |
| 2018/0071221 A1 | 3/2018 | Roberts et al. | |
| 2018/0263916 A1 | 9/2018 | Guo et al. | |

FOREIGN PATENT DOCUMENTS

| | | | |
|---|---|---|---|
| CA | 2659382 A1 | 1/2008 | |
| CA | 2356881 C | 2/2012 | |
| CN | 103463088 A | 12/2013 | |
| EP | 2046291 B1 | 1/2013 | |
| EP | 2032129 B1 | 1/2014 | |
| EP | 2012765 B1 | 3/2015 | |
| EP | 2040672 B1 | 4/2015 | |
| EP | 2351554 B1 | 9/2015 | |
| EP | 2724720 B1 | 2/2018 | |
| WO | WO-8503439 A * | 8/1985 | ........... A61K 31/165 |
| WO | 9408551 A2 | 4/1994 | |
| WO | 2004066978 A1 | 8/2004 | |
| WO | WO-2016044805 A1 * | 3/2016 | ........... A23L 33/105 |
| WO | WO-2016084099 A1 * | 6/2016 | ......... A61K 31/4402 |
| WO | 2017058836 A1 | 4/2017 | |
| WO | 2018183082 A1 | 10/2018 | |

OTHER PUBLICATIONS

Asghar "Pharmaceutical Technology Capsules," 2007 (Year: 2007).*

(Continued)

*Primary Examiner* — David J Blanchard
*Assistant Examiner* — Alissa Prosser
(74) *Attorney, Agent, or Firm* — Morrison & Foerster LLP

(57) ABSTRACT

The present disclosure provides for suspension-based pharmaceutical formulations for cold and flu medications, specifically suspension formulations and soft gel capsule dosage forms having reduced size. The present disclosure also provides methods of preparing the suspensions and soft gel capsule dosage forms.

30 Claims, 6 Drawing Sheets

(56) References Cited

OTHER PUBLICATIONS

Sigma "Particle size conversion table," accessed 2023; https://www.sigmaaldrich.com/US/en/support/calculators-and-apps/particle-size-conversion-table (Year: 2023).*
Gullapalli "Soft gelatin capsules," Journal of Pharmaceutical Sciences 99(10):4107-4148, 2010 (Year: 2010).*
Gullapalli et al. "Gelatin and non-gelatin capsule dosage forms," Journal of Pharmaceutical Sciences 106:1453-1465, 2017 (Year: 2017).*
International Preliminary Report on Patentability & Written Opinion in Related International Application PCT/US2019/032017 dated Nov. 26, 2020.
International Search Report and Written Opinion, dated Aug. 20, 2019, for PCT Patent Application No. PCT/US2019/032017, filed May 13, 2019, 8 pages.

\* cited by examiner

HIGH CONCENTRATION SUSPENSION FORMULATION FOR COLD AND FLU SOFT GEL CAPSULE MEDICATIONS

CROSS REFERENCE TO RELATED APPLICATIONS

This application claims priority to U.S. Provisional Application No. 62/672,457, filed May 16, 2018, and U.S. Provisional Application No. 62/816,727, filed Mar. 11, 2019, the disclosures of which are incorporated herein in their entirety.

FIELD OF THE INVENTION

The present disclosure relates generally to suspension-based pharmaceutical formulations for cold and flu medications, and more specifically to high-concentration suspension formulations and soft gel capsule dosage forms having reduced size, as well as methods of preparing the suspension formulations and soft gel capsules thereof.

BACKGROUND

The variety of symptoms of associated with cold and flu typically require multiple active pharmaceutical ingredients to treat each symptom separately. As such, over-the-counter cold and flu medications that combine several active ingredients in a single medication dosage are highly convenient and, therefore, attractive to consumers suffering from these multi-symptom ailments.

One area of interest in improving the attractiveness of cold and flu medications to consumers is modification of the size of these orally administered tablets/capsules. It is generally acknowledged that smaller dosage forms facilitate swallowing of the medication and, thus, provide a more pleasant experience to the consumer. Unfortunately, attempts to improve the attractiveness and palatability of all-in-one cold and flu medications to consumers have stagnated in recent years due to the difficulty of preparing new formulations that enable the size reduction of existing cold and flu medications without sacrificing other important attributes.

At present, there remains a need to find new formulations for cold and flu medications which allow for smaller dosage forms.

SUMMARY

The present disclosure addresses this need by providing a soft gel capsule comprising a suspension-based formulation, which allows for a smaller dosage form sizes of cold and flu soft gel capsule medications.

In one aspect, provided herein is a soft gel capsule comprising a suspension, wherein the suspension has a total volume of between 0.50 mL and 0.90 mL and the suspension comprises:
 between 300 mg and 400 mg acetaminophen;
 between 5 mg and 20 mg dextromethorphan HBr;
 between 2.5 mg and 10 mg phenylephrine HCl;
 optionally between 1 mg and 10 mg antihistamine;
 between 400 mg and 500 mg polyethylene glycol; and
 between 25 mg and 75 mg povidone.

In some embodiments, provided herein is a soft gel capsule comprising a suspension, wherein the suspension has a total volume of between 0.50 mL and 0.90 mL and the suspension comprises:
 between 300 mg and 400 mg acetaminophen;
 between 5 mg and 20 mg dextromethorphan HBr;
 between 2.5 mg and 10 mg phenylephrine HCl;
 optionally between 1 mg and 10 mg doxylamine succinate;
 between 400 mg and 500 mg polyethylene glycol; and
 between 25 mg and 75 mg povidone.

In other embodiments, the present disclosure provides a soft gel capsule comprising a suspension, wherein the suspension has a total volume of between 0.50 mL and 0.90 mL and the suspension comprises:
 between 300 mg and 400 mg acetaminophen;
 between 5 mg and 20 mg dextromethorphan HBr;
 between 2.5 mg and 10 mg phenylephrine HCl;
 optionally between 1 mg and 10 mg chlorpheniramine maleate;
 between 400 mg and 500 mg polyethylene glycol; and
 between 25 mg and 75 mg povidone.

In some embodiments, provided herein is a suspension, comprising:
 at least 400 mg/mL acetaminophen;
 at least 10.0 mg/mL dextromethorphan HBr;
 at least 5.00 mg/mL phenylephrine HCl;
 optionally at least 6.00 mg/mL doxylamine succinate;
 between 500 mg/mL and 700 mg/mL polyethylene glycol; and
 between 60 mg/mL and 80 mg/mL povidone.

In other embodiments, provided herein is a suspension, comprising:
 at least 400 mg/mL acetaminophen;
 at least 10.0 mg/mL dextromethorphan HBr;
 at least 5.00 mg/mL phenylephrine HCl;
 optionally at least 1.00 mg/mL chlorpheniramine maleate;
 between 500 mg/mL and 700 mg/mL polyethylene glycol; and
 between 60 mg/mL and 80 mg/mL povidone.

In another aspect, provided herein is a soft gel capsule comprising a suspension, wherein the suspension has a total volume of between 0.80 mL and 1.20 mL and the suspension comprises:
 between 300 mg and 400 mg acetaminophen;
 between 5 mg and 20 mg dextromethorphan HBr;
 between 2.5 mg and 10 mg phenylephrine HCl;
 between 100 mg and 300 mg guaifenesin;
 between 450 mg and 550 mg polyethylene glycol; and
 between 40 mg and 60 mg povidone.

In a further aspect, provided herein is a suspension, comprising:
 at least 250 mg/mL acetaminophen;
 at least 7.00 mg/mL dextromethorphan HBr;
 at least 2.00 mg/mL phenylephrine HCl;
 at least 100 mg/mL guaifenesin;
 between 400 mg/mL and 700 mg/mL polyethylene glycol; and
 between 30 mg/mL and 50 mg/mL povidone.

In another aspect, provided herein is a method for preparing a soft gel capsule, comprising:
 (a) combining polyethylene glycol and povidone to provide a mixture;
 (b) adding the acetaminophen to the mixture of step (a);
 (c) adding dextromethorphan HBr, phenylephrine HCl, polyethylene glycol, and optionally one or more further active pharmaceutical ingredients to the mixture of step (b) to provide a final mixture;
 (d) heating and stirring the final mixture;
 (e) cooling the final mixture to provide a suspension as an inner fill;

combining sorbitol-sorbitan solution, glycerin, water, one or more colorants and gelatin to provide an outer shell mixture;

(g) cooling the outer shell mixture; and
(h) encapsulating the suspension with the outer shell mixture of step (h) to provide the soft gel capsule.

In some embodiments, the one or more further active pharmaceutical ingredients is an antihistamine, an expectorant, or a combination thereof. In certain embodiments, the one or more further active pharmaceutical ingredients is selected from the group consisting of doxylamine succinate, chlorpheniramine maleate, and guaifenesin.

In still yet another aspect, the present disclosure provides a method for preparing a suspension, comprising:

(a) combining polyethylene glycol and povidone to provide a mixture;
(b) adding the acetaminophen to the mixture of step (a);
(c) adding dextromethorphan HBr, phenylephrine HCl, polyethylene glycol, and optionally one or more further active pharmaceutical ingredients to the mixture of step (b) to provide a final mixture;
(d) heating and stirring the final mixture; and
(e) cooling the final mixture to provide the suspension.

In some embodiments, the one or more further active pharmaceutical ingredients is an antihistamine, an expectorant, or a combination thereof. In certain embodiments, the one or more further active pharmaceutical ingredients is selected from the group consisting of doxylamine succinate, chlorpheniramine maleate, and guaifenesin.

DETAILED DESCRIPTION

Figure 1:
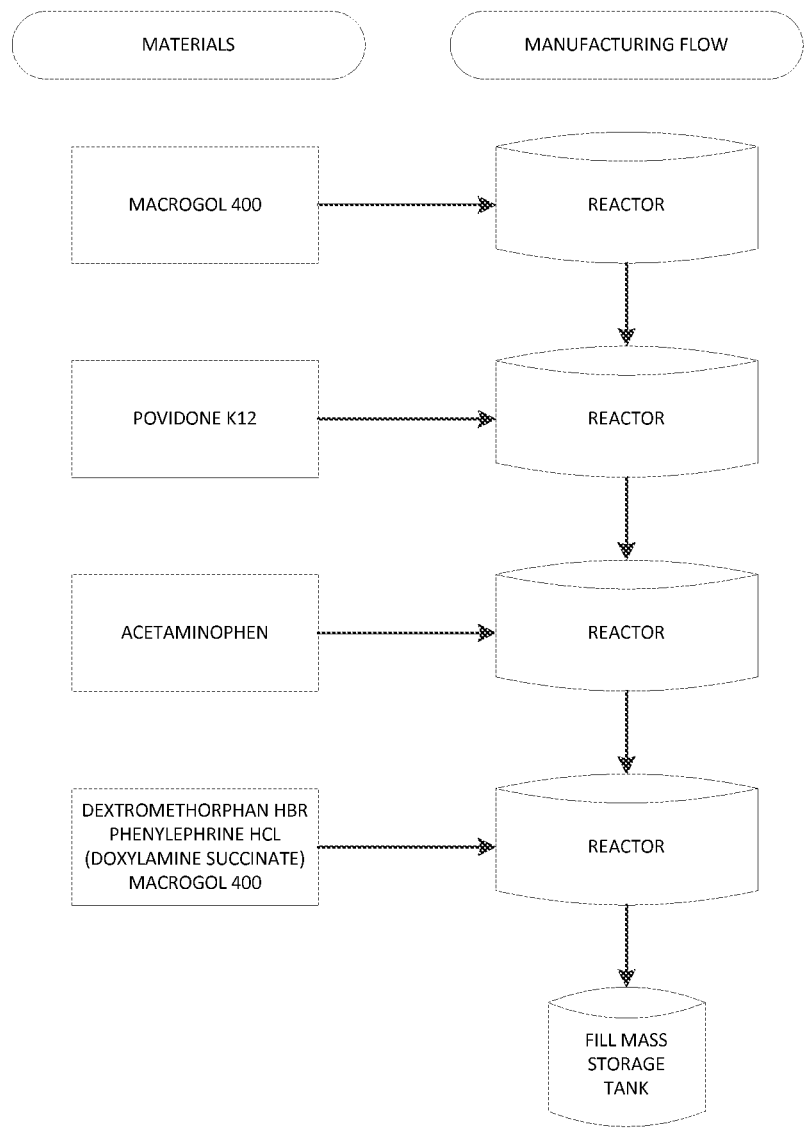
FIG. 1 depicts a process flow chart for preparing a suspension-based cold and flu formulation containing acetaminophen, dextromethorphan HBr, and phenylephrine HCl, and optionally also doxylamine succinate.

As a consequence of combining many active ingredients for treating cold and flu symptoms into a single dosage form, the composition of such medications should be carefully controlled to ensure the even distribution, proper dosage ratios, and stability of each active ingredient in the formulation during the manufacturing process. Many existing cold and flu medications are prepared as solution-based capsules with liquid formulations (i.e., liquid gels) whose properties have long been optimized for manufacturing consistency. Therefore, it is difficult to reduce the size of a liquid gel capsule size without also lowering the amount of each active ingredient present in the medication and resulting in a lesser therapeutic effect per liquid gel capsule.

Concentrated suspensions are one option to replace liquid formulations that could allow for a reduction in capsule size while maintaining therapeutic effect per capsule. However, suspension-based combination formulations are plagued by a number of processing issues including non-uniform dispersion of such suspensions having large ratios of active ingredients, phase separation during manufacture and storage, the instability of the active ingredients, etc. Moreover, suspension-based formulations, which are often cloudy or milky in appearance and contain particulate matter that visibly settles over time, can be aesthetically displeasing to the consumer. As a result, solution-based soft gel capsules are often preferred for their stability and translucent appearance. For these reason, solution-based liquid gels remain the dominant dosages form for cold and flu medications from both manufacturing and consumer standpoints.

Thus, there remains a need to find new formulations for cold and flu medications which allow for smaller, overall attractive dosage forms, while preserving therapeutic effectiveness per dose and avoiding many of the pitfalls associated with suspension manufacturing processes.

The present inventors have developed a soft gel capsule comprising a suspension-based inner fill that allows the soft gel capsule to be reduced in size significantly as compared to liquid gel capsules, while delivering the same therapeutic dose in a visually attractive form. More specifically, the present inventors have formulated a suspension for cold and flu medications that eliminates extraneous ingredients in the inner fill but which also successfully avoids the aforementioned processing and quality issues. The present disclosure provides for cold and flu medications in the form of soft gel capsules which comprise a suspension.

The below formulations have achieved a balance of even distribution, proper dosage ratios, and stability of the active pharmaceutical ingredients by including a sufficient amount of polyethylene glycol and povidone, and optionally also glycerin, to allow the active pharmaceutical ingredients to remain in suspension without the use of further excipients. In particular, it has been identified that using a combination of these excipients above a threshold amount stabilizes the suspension during processing and allows the active pharmaceutical ingredients used in cold and flu medications to maintain their chemical purity and therapeutic efficacy in each capsule throughout the lifetime of the capsule—including handling, storage/shelf life, and final administration.

Moreover, the soft gel capsules of the present disclosure further combine the suspension with an outer shell that contains a colorant, which, for example, may be a pearlescent pigment. Suspensions are not considered very attractive due to presence of the active ingredients floating around as particulate matter in the formulation. The use of a colored and/or opaque outer shell can conceal particles in the suspension that are otherwise highly distasteful to consumers. By combining the suspension of the present disclosure with a colored outer shell, the soft gel capsules described herein deliver the same therapeutic effect in a dosage form that is simultaneously stable, reduced in size, and visually appealing to the consumer.

The following description sets forth exemplary methods, parameters and the like. It should be recognized, however, that such description is not intended as a limitation on the scope of the present disclosure but is instead provided as a description of exemplary embodiments.

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

In one aspect, provided herein is a suspension formulation for cold and flu medications. In another aspect, the present disclosure provides a soft gel capsule comprising an inner fill and an outer shell, wherein the inner fill is a suspension. In certain embodiments, the present disclosure provides a soft gel capsule comprising an inner fill, an outer shell, and a coating, wherein the inner fill is a suspension.

By controlling both the types and amounts of excipients used to disperse active pharmaceutical ingredients, a stable, high-concentration suspension can be prepared. When used as the inner fill for a soft gel capsule, the high-concentration suspension allows for a smaller soft gel capsule to be manufactured for improved consumer appeal. The present disclosure provides a soft gel capsule comprising an inner fill, wherein the inner fill is a suspension, and the soft gel capsule has a reduced size. The reduced size of the soft gel capsule may be described by various physical attributes including, but not limited to, the capsule's physical volume, the total capsule weight, and/or active ingredient density.

In some embodiments, the reduced size of the soft gel capsule is defined by the overall physical volume of the soft gel capsule. In some embodiments, the soft gel capsule has an overall volume of less than or equal to about 1400 $mm^3$, less than or equal to about 1350 $mm^3$, less than or equal to about 1300 $mm^3$, less than or equal to about 1200 $mm^3$, less than or equal to about 1100 $mm^3$, or less than or equal to about 1000 $mm^3$. In certain embodiments, the soft gel capsule has an overall volume of at least about 600 $mm^3$, at least about 650 $mm^3$, or at least about 700 $mm^3$. In further embodiments, the soft gel capsule has an overall volume of about 950 $mm^3$. In other embodiments, the soft gel capsule has an overall volume of about 1350 $mm^3$. It should be recognized that the overall volume of the soft gel capsule may be alternatively measured in $mm^3$, as described above, or in milliliters using appropriate unit conversion (0.1 mL=100 $mm^3$).

In other embodiments, the reduced size of the soft gel capsule may be represented by the total weight of the soft gel capsule. In some embodiments, the total weight of the soft gel capsule is less than about 1700 mg, less than about 1600 mg, less than about 1575 mg, less than about 1550 mg, less than about 1525 mg, less than about 1500 mg, less than about 1475 mg, less than about 1450 mg, less than about 1425 mg, less than about 1400 mg, less than about 1375 mg, less than about 1350 mg, less than about 1325 mg, less than about 1300 mg, less than about 1275 mg, less than about 1250 mg, less than about 1225 mg, less than about 1200 mg, less than about 1175 mg, or less than about 1150 mg. In certain embodiments, the total weight of the soft gel capsule is less than about 1150 mg. In other embodiments, the total weight of the soft gel capsule is less than about 1250 mg or less than about 1200 mg. In other embodiments, the total weight of the soft gel capsule is less than 1600 mg, less than about 1575 mg, less than about 1550 mg, or less than about 1525 mg. In certain embodiments, the total weight of the soft gel capsule is less than about 1575 mg or about 1550 mg. In some embodiments, the total weight of the soft gel capsule is about 1100 mg, about 1120 mg, about 1125 mg, about 1130 mg, about 1140 mg, or about 1150 mg. In other embodiments, the total weight of the soft gel capsule is about 1200 mg, about 1220 mg, about 1225 mg, about 1230 mg, about 1240 mg, or about 1250 mg. In yet other embodiments, the total weight of the soft gel capsule is 1520 mg, about 1530 mg, about 1540 mg, about 1550 mg, about 1560 mg, about 1570 mg, about 1580 mg, about 1590 mg, about 1600 mg, about 1650 mg, about 1660 mg, about 1670 mg, about 1680 mg, about 1690 mg, or about 1700 mg.

In still yet other embodiments, the soft gel capsule may be characterized by standard shape and size categories known in the art to describe soft gel capsule forms and fill values. In some embodiments, the soft gel capsule may have a shape that is oval, oblong, or round. In certain embodiments, the soft gel capsule may have a size between 12 and 18. In some embodiments, the soft gel capsule has a size of less than or equal to an oval, oblong, or round size 12 gel capsule. In certain embodiments, the soft gel capsule has a size and shape of 12 oval or 12 oblong. In some embodiments, the soft gel capsule has a size and shape of 12 oblong. In other embodiments, the soft gel capsule has a size of less than or equal an oval, oblong, or round size 18 capsule. In certain embodiments, the soft gel capsule has a size and shape of 18 oval or 18 oblong. In still other embodiments, the soft gel capsule has a size and shape of 18 oblong.

Notably, the suspension of the soft gel capsule does not contain added water as an excipient, which allows for the reduced size of the overall capsule and adds to the stability of the suspension. Therefore, all of the water contained within the soft gel capsule is derived from water added to the outer shell of the soft gel capsule, or adventitious water which migrates from the outer shell into the suspension during encapsulation and/or drying of the soft gel capsules. In some embodiments, the soft gel capsule comprises water. In some embodiments, the soft gel capsule comprises between about 20 mg and about 90 mg water. In certain embodiments, the soft gel capsule comprises about 80 mg water. In other embodiments, the soft gel capsule comprises about 90 mg water.

In some embodiments, the soft gel capsule has a water content between about 1.5 wt % and about 7.5 wt % of the total weight of the soft gel capsule. In some embodiments, the soft gel capsule has a water content of less than about 7.0 wt %.

In addition to allowing for reduced capsule size, the low water content of the soft gel capsules described herein may also be beneficial to minimizing microbial growth and, consequently, prolonging the shelf-life of the soft gel capsules. The water content of the soft gel capsules may be described by water activity in relation to their reduced susceptibility to microbial growth. For example, in some embodiments, the soft gel capsules of the present disclosure have a water activity of between about 0.40 and about 0.50, between about 0.40 and about 0.45, between about 0.45 and about 0.50, or between about 0.41 and about 0.45.

Inner Fill (Suspension)

The size of soft gel capsules as described herein is dependent upon composition the inner fill of the capsule, which contains active pharmaceutical ingredients to treat cold and flu symptoms, and polyethylene glycol and povidone, and optionally glycerin, as excipients. The soft gel capsules of the present disclosure comprising a suspension and having a reduced size may be differentiated from existing liquid gel capsules in that the suspension contains select excipients in quantities sufficient to stably suspend an equivalent amount of active pharmaceutical ingredients within the reduced volume of the suspension. If insufficient quantities of the polyethylene glycol, povidone, or glycerin are used or extraneous excipients are included, the excipients may not provide an adequately stable suspension with proper dosage ratios of the active pharmaceutical ingredients to allow for consistent manufacturing and long product life. Conversely, if excess quantities of the excipients are used, the resulting solution formulation may be stable and easy to process into gel capsules but the improvement in stability is achieved at the expense of size reductions to the soft gel capsules.

The selection of each excipient and the amounts used in the suspension are influenced by the type and quantity of active pharmaceutical ingredients in the cold and flu medication. The particular selection of active pharmaceutical ingredients in the cold and flu medication will depend upon the symptoms experienced by the consumer. To provide relief from symptoms during waking hours, daytime formulations may contain acetaminophen, dextromethorphan HBr, and phenylephrine HCl as active pharmaceutical ingredients. One or more further active pharmaceutical ingredients may be added to the formulation containing acetaminophen, dextromethorphan HBr, and phenylephrine HCl as desired. For example, if additional relief from cough and congestion are needed, the cold and flu formulation may contain a combination of guaifenesin, acetaminophen, dextromethorphan HBr, and phenylephrine HCl. If cold and flu symptoms interfere with one's ability to sleep, formulations may be modified to further include an additional agent as a sleep aid. As such, nighttime formulations may contain acetaminophen, dextromethorphan HBr, and phenylephrine HCl, similar to the daytime formulation, but with the addition of doxylamine succinate or chlorpheniramine maleate as a further active pharmaceutical ingredient.

The therapeutic effect provided by the daytime and nighttime formulations depends on the amounts of the active ingredients in the final soft gel capsule dosage form. Therefore, the therapeutic effect of the soft gel capsules depends upon how much of each active pharmaceutical ingredient can be delivered in the reduced volume of the suspension. In certain embodiments, the inner fill is a high-concentration suspension. In one aspect, the present disclosure relates to suspension-based formulations for cold and flu medications. In some embodiments, the present disclosure provides a soft gel capsule comprising an inner fill, wherein the inner fill is a suspension and the suspension comprises active pharmaceutical ingredients and excipients.

As described herein, the terms "suspension" or "high-concentration suspension" may be used interchangeably and can refer alternately to a standalone composition or to the inner fill component, which can be encapsulated, for example, by an outer shell, in a soft gel capsule. As understood in the art, a suspension is a biphasic preparation consisting of solid particles dispersed throughout a liquid phase. For pharmaceutical compositions, a common type of suspension contains solid particles of one or more active pharmaceutical ingredients suspended throughout a liquid medium of one or more excipients. It should be recognized when an active pharmaceutical ingredient is indicated as "in suspension" or "suspended", at least a portion of the active pharmaceutical ingredient is undissolved in the primary medium of the excipients. For example, in some embodiments, the suspension comprises at least one active pharmaceutical in suspension. In some embodiments, the suspension comprises at least two active pharmaceutical ingredients in suspension. In certain embodiments wherein the suspension comprises three or more active pharmaceutical ingredients, the suspension comprises at least three active pharmaceutical ingredients in suspension. In certain embodiments wherein the suspension comprises four or more active pharmaceutical ingredients, the suspension comprises at least four active pharmaceutical ingredients in suspension.

Depending upon the maximum solubility of each active pharmaceutical ingredient in the chosen excipients and the quantity of the excipients, some active ingredients may be completely dissolved (i.e., exist in solution) while others are entirely undissolved/suspended (i.e. exist in suspension) or are partially dissolved/partially suspended (i.e., a fraction exists in solution and the remaining fraction exists in suspension). It should be understood that the suspension as described herein may encompass all possible combinations of the suspension having some pharmaceutical ingredients in solution, or in suspension, or in partial suspension, provided that at least one active pharmaceutical ingredient is partially or entirely suspended. In some embodiments, at least a portion of at least one active pharmaceutical ingredient is suspended. In certain embodiments, at least a portion each of at least two active pharmaceutical ingredients is suspended. In still other embodiments, at least a portion each of at least three active pharmaceutical ingredients is suspended. In some embodiments, at least a portion each of at least four active pharmaceutical ingredients is suspended.

In some embodiments, the suspension comprises acetaminophen, wherein at least a portion of the acetaminophen is in suspension. In other embodiments, the suspension comprises dextromethorphan HBr, wherein at least a portion of the dextromethorphan HBr is in suspension. In yet other embodiments, the suspension comprises phenylephrine HCl, wherein at least a portion of the phenylephrine HCl is in suspension. In still other embodiments, the suspension comprises doxylamine succinate, wherein at least a portion of the doxylamine succinate is in suspension. In some embodiments, the suspension comprises chlorpheniramine maleate, wherein at least a portion of the chlorpheniramine maleate is in suspension. In yet other embodiments, the suspension comprises guaifenesin, wherein at least a portion of the guaifenesin is in suspension.

For active pharmaceutical ingredients that are partially suspended, the amount of active pharmaceutical ingredient in suspension can be described as a percentage of the total amount of the active pharmaceutical ingredient. In some embodiments, at least about 60%, at least about 70%, at least about 75%, at least about 80%, at least about 85%, at least about 90%, at least about 92%, at least about 95%, or at least about 97% of the active pharmaceutical ingredient is suspended. It should be recognized that the percentage of each active pharmaceutical ingredient in suspension is independent of the percentages of the other active pharmaceutical ingredients in suspension.

It is desirable that the majority of the active pharmaceutical ingredients are suspended rather than dissolved, as the quantity of excipients should be controlled to avoid excess excipient, and thereby excess volume, in the inner fill. In other embodiments, the inner fill is not a solution. In contrast to a suspension, it should be recognized that "a solution" as described herein is intended to encompass a homogeneous mixture of two or more components in which all components exist in the same liquid phase—i.e., the minor components such as active ingredients are completely dissolved within the primary dispersion medium (excipients).

In some instances, a suspension may be readily distinguished from a solution by the characteristics of the active ingredient particles distributed throughout the excipient medium. Qualitatively, a suspension may be identified by the opacity of the suspension or the presence of particles of active pharmaceutical ingredients that are visually apparent. In some embodiments, the suspension is translucent. In other embodiments, the suspension is opaque. In certain embodiments, the suspension is not transparent.

The suspension may also be differentiated from a solution in that it contains particles. These particles may be further characterized as having a particle size within a defined particle size range, an average particle size above a certain threshold particle size, or a particular particle size distribution. In addition to being useful to characterize a suspension, the particle size properties of the active ingredients may further influence the physical properties of the suspension, including uniformity of dispersion and stability. As such, the particle size ranges and distributions within those ranges for each active pharmaceutical ingredient may be varied to achieve the balance of dispersion and stability. In some embodiments, the suspension comprises active pharmaceutical ingredients, wherein at least one active pharmaceutical ingredient is in suspension and wherein the at least one active pharmaceutical ingredient in suspension has an average particle size of less than about 250 microns. In some embodiments of the foregoing, the suspension comprises active pharmaceutical ingredients, wherein at least one active pharmaceutical ingredient is in suspension and wherein the at least one active pharmaceutical ingredient in suspension has an average particle size of at least about 50 microns.

The present disclosure provides a soft gel capsule comprising a suspension as an inner fill that delivers the same therapeutic effect, i.e. dosage amount, for each active pharmaceutical ingredient as typically achieved with liquid gels but with a reduced inner fill volume and therefore, also a reduced capsule size. As such, the soft gel capsules of the present disclosure may be described with respect to the total volume (mL) of the suspension used as the inner fill on a per capsule basis. In some embodiments, the soft gel capsule comprises a suspension, wherein the suspension has a total volume of between about 0.50 mL and about 1.50 mL, between about 0.50 mL and about 1.20 mL, between about 0.50 mL and about 1.00 mL, between about 0.50 mL and about 0.90 mL, between about 0.80 mL and about 1.20 mL, between about 0.80 mL and about 1.00 mL, between about 0.90 mL and about 1.20 mL, between about 1.00 mL and about 1.20 mL, between about 0.60 mL and about 0.80 mL, or between about 0.70 mL and about 0.75 mL. In some embodiments, the suspension has a total volume at least about 0.50 mL, or at least about 0.60 mL. In other embodiments, the suspension has a total volume of less than about 1.50 mL, less than about 1.20 mL, less than about 1.00 mL, less than about 0.90 mL, or less than about 0.80 mL.

It should be recognized, however, that the total of volume of suspension in the soft gel capsule will reflect the number of active pharmaceutical ingredients in the medication as well as the doses of each active in the soft gel capsule. For example, in some embodiments wherein the soft gel capsule comprises acetaminophen, dextromethorphan HBr, phenylephrine, and optionally an antihistamine (e.g., doxylamine succinate or chlorpheniramine maleate), the suspension has a total volume of about 0.71 mL or about 0.72 mL. In other embodiments wherein the soft gel capsule comprises acetaminophen, dextromethorphan HBr, phenylephrine, and guaifenesin, the suspension has a total volume of about 0.95 mL, about 1.00 mL, about 1.10 mL or about 1.20 mL.

As described above, the reduced size of the soft gel capsule is achieved by eliminating extraneous excipients used in the suspension. However, additional active or inactive ingredients may be included in the suspensions used for daytime and nighttime formulations as long as they do not substantially affect the overall volume or stability of the suspension and, consequently, the size of the soft gel capsule.

In some embodiments, the suspension consists essentially of active pharmaceutical ingredients and excipients as described herein. In certain embodiments, the suspension consists essentially of acetaminophen, dextromethorphan HBr, phenylephrine HCl, polyethylene glycol, and povidone. In certain other embodiments, the suspension consists essentially of acetaminophen, dextromethorphan HBr, phenylephrine HCl, doxylamine succinate, polyethylene glycol, and povidone. In some embodiments, the suspension consists essentially of acetaminophen, dextromethorphan HBr, phenylephrine HCl, chlorpheniramine maleate, polyethylene glycol, and povidone. In other embodiments, the suspension consists essentially of guaifenesin, acetaminophen, dextromethorphan HBr, phenylephrine HCl, polyethylene glycol, and povidone. In yet further embodiments, the suspension consists of acetaminophen, dextromethorphan HBr, phenylephrine HCl, polyethylene glycol and povidone. In yet another embodiment, the suspension consists of acetaminophen, dextromethorphan HBr, phenylephrine HCl, doxylamine succinate, polyethylene glycol and povidone. In some embodiments, the suspension consists of guaifenesin, acetaminophen, dextromethorphan HBr, phenylephrine HCl, polyethylene glycol and povidone. In other embodiments, the suspension consists of acetaminophen, dextromethorphan HBr, phenylephrine HCl, chlorpheniramine maleate, polyethylene glycol and povidone.

Active Pharmaceutical Ingredients (APIs)

Common cold and flu symptoms include pain, fever, sinus congestion, and cough. As such, most commercial cold and flu medications contain a combination of an analgesic, an antipyretic, nasal decongestant, and cough suppressant. In some embodiments of the foregoing, the suspension comprises acetaminophen as an analgesic/antipyretic. In other embodiments, the suspension comprises dextromethorphan or a pharmaceutically acceptable salt thereof, as a cough suppressant. In certain embodiments, the suspension comprises dextromethorphan hydrobromide, or dextromethorphan HBr. In further embodiments, the suspension comprises phenylephrine or a pharmaceutically acceptable salt thereof, as a nasal decongestant. In certain embodiments, the suspension comprises phenylephrine hydrochloride, or phenylephrine HCl.

For nighttime formulations, an antihistamine or other sleep-inducing agent may be included in the suspension. In some embodiments, the suspension comprises doxylamine or a pharmaceutically acceptable salt thereof, as an antihistamine. In certain embodiments, the suspension comprises doxylamine succinate. In other embodiments, the suspension comprises chlorpheniramine or a pharmaceutically acceptable salt thereof. In certain embodiments, the suspension comprises chlorpheniramine maleate.

It should be recognized that the suspensions and soft gel capsules of the present disclosure may also be suitable to deliver combinations of cold and flu medications, wherein one or more of the above analgesic/antipyretic, nasal decongestant, cough suppressant and antihistamine active pharmaceutical ingredients is substituted with a therapeutically equivalent active ingredient. Such combinations may include, for example, naproxen or ibuprofen as analgesics/antipyretics in place of acetaminophen, pseudoephedrine as a nasal decongestant in lieu of phenylephrine, or diphenhydramine or chlorpheniramine as antihistamines instead of doxylamine succinate, or any combinations thereof.

In addition, it should also be recognized that additional active pharmaceutical ingredients that are useful in the treatment of cold and flu symptoms, such as guaifenesin as an expectorant or caffeine as an analgesic adjuvant/pain reliever aid, may be added to the suspensions described herein provided that the addition of said actives does not deleteriously affect the stability of the suspension. For example, in some embodiments, the suspension comprises guaifenesin.

Depending on the desired therapeutic effect to be provided by the soft gel capsule—that is, the extent to which the cold and flu symptoms are alleviated and how long relief is provided, the quantities of the active pharmaceutical ingredients contained in the suspension may vary. This, in turn, affects the ranges for acceptable quantities of excipients to be used to provide a stable, uniform suspension, which consequently affects the overall size of the capsule.

The quantity of the active pharmaceutical ingredients present in the suspension may be expressed in terms of absolute milligram amounts. It should be recognized that the absolute milligram amounts of the present disclosure are intended to indicate the quantity of the active pharmaceutical ingredients in the suspension or inner fill of a soft gel on a per capsule basis. The quantity of the active pharmaceutical ingredients in the suspension may also be represented as a concentration of milligrams per milliliter (mg/mL) of the suspension.

Alternatively, the quantity of the active pharmaceutical ingredients may also be expressed as a weight percentage of the total weight of the suspension or as a weight percentage of the total weight of the soft gel capsule.

Acetaminophen

Acetaminophen may be included in the present combination formulations as an analgesic/antipyretic agent to treat fever or pain related to cold and flu. In some embodiments, the suspension comprises about 150 mg, about 200 mg, about 300 mg, about 325 mg, about 400 mg, or about 500 mg acetaminophen. In certain embodiments, the suspension comprises about 325 mg acetaminophen. In some embodiments, the suspension comprises at least about 150 mg, at least about 200 mg, or at least about 300 mg acetaminophen. In certain embodiments, the suspension comprises at least about 300 mg acetaminophen. In other embodiments, the suspension comprises less than or equal to about 500 mg, less than or equal to about 450 mg, or less than or equal to about 400 mg acetaminophen.

In some embodiments, the suspension comprises at least about 250 mg/mL, at least about 300 mg/mL, at least about 325 mg/mL, at least about 350 mg/mL, at least about 375 mg/mL, at least about 400 mg/mL, at least about 425 mg/mL, or at least about 450 mg/mL acetaminophen. In other embodiments, the suspension comprises between about 300 mg/mL and about 700 mg/mL, between about 300 mg/mL and about 400 mg/mL, between about 400 mg/mL and about 500 mg/mL, between about 450 mg/mL and about 500 mg/mL, or between about 425 mg/mL and about 475 mg/mL acetaminophen. In certain embodiments, the suspension comprises between about 400 mg/mL and about 500 mg/mL, between about 400 mg/mL and about 450 mg/mL, between about 450 mg/mL and about 500 mg/mL, or between about 425 mg/mL and about 475 mg/mL acetaminophen.

In other embodiments wherein the acetaminophen is employed as an analgesic/antipyretic, the suspension comprises at least about 25 wt %, at least about 27 wt %, at least about 29%, at least about 34 wt %, at least about 36 wt % at least about 38 wt %, at least about 38.2 wt %, at least about 38.4 wt %, or at least about 38.6 wt % acetaminophen of the total weight of the suspension. In other embodiments, the suspension comprises between about 25 wt % and about 40 wt %, between about 25 wt % and about 30 wt %, between about 38.4 wt % and about 38.7 wt %, between about 38.2 wt % and about 38.8 wt % acetaminophen or between about 38 wt % and 39 wt % acetaminophen of the total weight of the suspension. In some embodiments, the suspension comprises about 38.4 wt %, about 38.6 wt %, or about 38.7 wt % acetaminophen of the total weight of the suspension. In certain embodiments, the suspension comprises about 38.4 wt % acetaminophen of the total weight of the suspension. In yet other embodiments, the suspension comprises about 38.7 wt % acetaminophen of the total weight of the suspension. In still yet other embodiments, the suspension comprises about 25.0 wt %, about 27.0 wt %, about 29.0 wt %, or about 30.0 wt % acetaminophen of the total weight of the suspension.

In some embodiments of the present disclosure, wherein a soft gel capsule comprises the suspension as an inner fill and the suspension comprises acetaminophen, acetaminophen is at least about 18.0 wt %, at least about 20.0 wt %, at least about 21.0 wt %, at least about 22.0 wt %, at least about 24.0 wt %, at least about 26.0 wt %, at least about 28.0 wt %, at least about 28.5 wt %, at least about 28.7 wt %, or at least about 28.9 wt % of the total weight of the soft gel capsule. In other embodiments, acetaminophen is between about 18.0 wt % and about 24.0 wt %, between about 20.0 wt % and about 22.0 wt %, between about 28.0 wt % and about 30.0 wt %, between about 28.5 wt % and about 29.5 wt %, or between about 28.7 wt % and about 29.0 wt % of the total weight of the soft gel capsule. In yet other embodiments, acetaminophen is about 28.8 wt % or about 28.9 wt % of the total weight of the soft gel capsule. In still yet other embodiments, acetaminophen is about 21.3 wt % or about 21.4 wt % of the total weight of the soft gel capsule.

It should also be recognized that the suspensions of the present disclosure may comprise alternative analgesic/antipyretic active ingredients as therapeutically equivalent substitutes for acetaminophen. For example, in some embodiments, the suspension comprises naproxen or ibuprofen in place of acetaminophen at a therapeutically equivalent amount.

Dextromethorphan

Dextromethorphan hydrobromide may be added to the suspension formulation as an antitussive to suppress cough. In some embodiments, the suspension comprises about 5 mg, about 10 mg, about 15, mg, about 20 mg, about 25 mg, or about 30 mg dextromethorphan HBr. In certain embodiments, the suspension comprises about 10 mg dextromethorphan HBr. In some embodiments, the suspension comprises at least about 5 mg, at least about 10 mg, at least about 15 mg, or at least about 20 mg dextromethorphan HBr. In certain embodiments, the suspension comprises at least about 5 mg or at least about 10 mg dextromethorphan HBr. In other embodiments, the suspension comprises less than or equal to about 30 mg or less than or equal to about 25 mg dextromethorphan HBr.

In some embodiments, the suspension comprises at least about 7.00 mg/mL, at least about 8.00 mg/mL, at least about 10.0 mg/mL, at least about 12.0 mg/mL, or at least about 14.0 mg/mL dextromethorphan HBr. In certain embodiments, the suspension comprises about 14.0 mg/mL dextromethorphan HBr. In other embodiments, the suspension comprises between about 7.00 mg/mL and about 20.0 mg/mL, between about 7.00 mg/mL and about 15.0 mg/mL, between about 7.00 mg/mL and about 10.0 mg/mL, between about 10.0 mg/mL and about 15.0 mg/mL, between about 15.0 mg/mL and about 20.0 mg/mL, or between about 12.0 mg/mL and about 16.0 mg/mL dextromethorphan HBr. In certain embodiments, the suspension comprises between about 7.00 mg/mL and about 10.0 mg/mL or between about 10.0 mg/mL and about 15.0 mg/mL dextromethorphan HBr.

In some embodiments in which dextromethorphan HBr is added as a cough suppressant, the suspension comprises at least about 0.8 wt %, at least about 0.9 wt %, at least about 1.0 wt %, or at least about 1.2 wt % dextromethorphan HBr of the total weight of the suspension. In other embodiments, the suspension comprises between about 0.8 wt % and about 1.2 wt %, between about 0.9 wt % and about 1.3 wt %, between about 1.0 wt % and about 1.2 wt %, or between about 1.1 wt % and about 1.2 wt % dextromethorphan HBr of the total weight of the suspension. In certain embodiments, the suspension comprises between about 1.1 wt % and about 1.2 wt % dextromethorphan HBr. In still yet other embodiments, the suspension comprises about 1.1 wt % or about 1.2 wt % dextromethorphan HBr of the total weight of the suspension. In some embodiments, the suspension comprises about 0.8 wt % or about 0.9 wt % dextromethorphan HBr.

In some embodiments of the soft gel capsules described herein, wherein the soft gel capsule comprises a suspension as an inner fill and the suspension comprises dextromethorphan HBr, dextromethorphan HBr is at least about 0.50 wt %, at least about 0.60 wt %, at least about 0.65 wt %, at least about 0.70 wt %, at least about 0.80 wt %, at least about 0.85 wt %, or at least about 0.87 wt %, of the total weight of the soft gel capsule. In other embodiments, dextromethorphan HBr is between about 0.60 wt %, and about 1.00 wt %, between about 0.60 wt % and about 0.70 wt %, between about 0.80 wt % and about 1.00 wt %, between about 0.85 wt % and about 0.95 wt %, or between about 0.85 wt % and about 0.90 wt % of the total weight of the soft gel capsule. In certain embodiments, dextromethorphan HBr is between about 0.80 wt % and about 0.90 wt % or between about 0.85 wt % and about 0.90 wt % of the total weight of the soft gel capsule. In other embodiments, dextromethorphan HBr is between about 0.60 wt % and about 0.70 wt % of the total weight of the soft gel capsule.

As with acetaminophen, it should be recognized that the dextromethorphan of the suspension may be substituted with an alternative cough suppressant at a therapeutically equivalent amount.

Phenylephrine

Phenylephrine HCl may be included in the suspension of the soft gel capsule as a nasal decongestant to provide relief from sinus congestion. In some embodiments, the suspension comprises about 2.5 mg, about 5 mg, about 7.5 mg, about 10 mg, about 15 mg, or about 20 mg phenylephrine HCl. In certain embodiments, the suspension comprises about 5 mg phenylephrine HCl. In some embodiments, the suspension comprises at least about 2.5 mg, at least about 5 mg, at least about 10 mg, or at least about 15 mg phenylephrine HCl. In certain embodiments, the high concentration suspension comprises at least about 5 mg phenylephrine HCl. In some embodiments, the suspension comprises less than or equal to about 25 mg or less than or equal to about 20 mg phenylephrine HCl.

In some embodiments, the suspension comprises at least about 2.00 mg/mL, at least about 4.00 mg/mL, at least about 5.00 mg/mL, at least about 5.50 mg/mL, at least about 6.00 mg/mL, at least about 6.50 mg/mL, at least about 7.00 mg/mL, at least about 7.50 mg/mL, or at least about 8.00 mg/mL phenylephrine HCl. In certain embodiments, the suspension comprises at least about 6.50 mg/mL, at least about 7.00 mg/mL or at least about 7.50 mg/mL phenylephrine HCl. In other embodiments, the suspension comprises between about 2.00 mg/mL and about 8.00 mg/mL, between about 5.00 mg/mL and about 8.00 mg/mL, between about 5.00 mg/mL and about 7.00 mg/mL, between about 6.00 mg/mL and about 8.00 mg/mL, or between about 6.00 mg/mL and about 7.00 mg/mL phenylephrine HCl.

In some embodiments, the suspension comprises at least about 0.40 wt %, at least about 0.42 wt %, at least about 0.44 wt %, at least about 0.46 wt %, at least about 0.48 wt %, at least about 0.50 wt %, at least about 0.55 wt %, or at least about 0.59 wt % phenylephrine HCl of the total weight of the suspension. In certain embodiments, the suspension comprises at least about 0.59 wt % phenylephrine HCl of the total weight of the suspension. In other embodiments, the suspension comprises between about 0.40 wt % and about 0.60 wt %, between about 0.40 wt % and about 0.50 wt %, between about 0.42 wt % and about 0.46 wt %, between about 0.50 wt % and about 0.65 wt %, between about 0.50 wt % and about 0.60 wt %, between about 0.54 wt % and about 0.64 wt %, or between about 0.58 wt % and about 0.62 wt % phenylephrine HCl of the total weight of the suspension. In certain embodiments, the suspension comprises about 0.59 wt % or about 0.60 wt % phenylephrine HCl of the total weight of the suspension. In other embodiments, the suspension comprises about 0.44 wt % or about 0.45 wt % of the total weight of the suspension.

In some embodiments of the soft gel capsules described herein, phenylephrine HCl is at least about 0.30 wt %, at least about 0.32 wt %, at least about 0.34 wt %, at least about 0.36 wt % at least about 0.38 wt %, at least about 0.40 wt %, at least about 0.42 wt %, or at least about 0.44 wt % of the total weight of the soft gel capsule. In certain embodiments, phenylephrine HCl is at least about 0.43 wt %, at least about 0.44 wt %, or at least about 0.45 wt % of the total weight of the soft gel capsule. In certain other embodiments, phenylephrine HCl is at least about 0.30 wt %, at least about 0.32 wt %, at least about 0.34 wt % of the total weight of the soft gel capsule. In other embodiments, phenylephrine HCl is between about 0.30 wt % and about 0.50 wt %, between about 0.30 wt % and about 0.40 wt %, between about 0.30 wt % and about 0.34 wt %, between about 0.32 wt % and about 0.34 wt %, about 0.40 wt % and about 0.48 wt %, between about 0.42 wt % and about 0.46 wt %, or between about 0.43 wt % and about 0.46 wt %, between about 0.43 wt % and about 0.45 wt % of the total weight of the soft gel capsule. In certain embodiments, phenylephrine HCl is between about 0.44 wt % and about 0.45 wt % of the total weight of the soft gel capsule. In yet other embodiments, phenylephrine HCl is about 0.44 wt % or about 0.45 wt % of the total weight of the soft gel capsule. In still yet other embodiments, phenylephrine HCl is about 0.32 wt % or about 0.33 wt % of the total weight of the soft gel capsule.

As with acetaminophen and dextromethorphan above, the suspensions of the present disclosure may utilize alternative nasal decongestants in lieu of phenylephrine. For example, in some embodiments, the suspension comprises pseudoephedrine in place of phenylephrine in a therapeutically equivalent amount.

Doxylamine

The suspensions as described above may further contain the antihistamine doxylamine to promote sleep, for example, in nighttime formulations. In certain embodiments wherein the suspension comprises doxylamine succinate, the suspension comprises about 5 mg, about 6 mg, about 6.25 mg, about 6.5 mg, or about 7 mg doxylamine succinate. In certain embodiments, the suspension comprises about 6.25 mg doxylamine succinate. In some embodiments, the suspension comprises at least about 5 mg, at least about 6 mg, at least about 6.25 mg, or at least about 6.5 mg doxylamine succinate.

In some embodiments, the suspension comprises at least about 6.00 mg/mL, at least about 6.50 mg/mL, at least about 7.00 mg/mL, at least about 7.50 mg/mL, at least about 8.00 mg/mL, or at least 8.50 mg/mL doxylamine succinate. In certain embodiments, the suspension comprises at least about 6.00 mg/mL or at least about 8.50 mg/mL doxylamine succinate. In other embodiments, the suspension comprises between about 6.00 mg/mL and about 10.0 mg/mL, between about 7.00 mg/mL and about 9.00 mg/mL, between about 8.00 mg/mL and about 10.0 mg/mL, or between about 8.00 mg/mL and about 9.00 mg/mL doxylamine succinate. In certain embodiments, the suspension comprises between about 8.00 mg/mL and about 9.00 mg/mL doxylamine succinate.

In some embodiments, the suspension comprises at least about 0.65 wt %, at least about 0.70 wt %, at least about 0.72 wt %, or at least about 0.74 wt % doxylamine succinate of the total weight of the suspension. In certain embodiments, the suspension comprises at least about 0.72 wt %, at least about 0.73 wt %, or at least about 0.74 wt % doxylamine succinate of the total weight of the suspension. In other embodiments, the suspension comprises between about 0.70 wt % and about 0.78 wt %, between about 0.72 wt % and about 0.76 wt %, or between about 0.73 wt % and about 0.75 wt % doxylamine succinate of the total weight of the suspension. In certain embodiments, the suspension comprises between about 0.73 wt % and about 0.75 wt % doxylamine succinate of the total weight of the suspension. In yet further embodiments, the suspension comprises about 0.73 wt %, about 0.74 wt %, or about 0.75 wt % doxylamine succinate of the total weight of the suspension.

In some embodiments, doxylamine succinate is at least about 0.50 wt %, at least about 0.52 wt %, at least about 0.54 wt %, or at least about 0.56 wt % of the total weight of the soft gel capsule. In certain embodiments, doxylamine succinate is at least about 0.54 wt %, at least about 0.55 wt %, or at least about 0.56 wt % of the total weight of the soft gel capsule. In other embodiments, doxylamine succinate is between about 0.50 wt % and about 0.60 wt %, between about 0.52 wt % and about 0.58 wt %, or between about 0.54 wt % and about 0.56 wt % of the total weight of the soft gel capsule. In certain embodiments, doxylamine succinate is between about 0.54 wt % and about 0.56 wt % of the total weight of the soft gel capsule. In yet other embodiments, doxylamine succinate is about 0.54 wt %, about 0.55 wt %, or about 0.56 wt % of the total weight of the soft gel capsule.

Similar to acetaminophen, dextromethorphan, and phenylephrine above, the doxylamine succinate of the suspension may be substituted with alternative antihistamines known in the art. For example, in some embodiments, the suspension comprises chlorpheniramine or diphenhydramine in place of doxylamine succinate in a therapeutically equivalent amount.

Chlorpheniramine

As described above, the active pharmaceutical ingredients used in the suspension-based cold and flu combination medication may be substituted with equivalent actives. For example, the suspensions described herein may contain the antihistamine chlorpheniramine in lieu of doxylamine to promote sleep in nighttime formulations. In some embodiments, the suspension of the present disclosure comprises chlorpheniramine or a pharmaceutically acceptable salt thereof. In certain embodiments, the suspension comprises chlorpheniramine maleate.

In some embodiments wherein the suspension comprises chlorpheniramine maleate, the suspension comprises about 1 mg, about 2 mg, or about 5 mg chlorpheniramine maleate. In certain embodiments the suspension comprises about 2 mg chlorpheniramine maleate. In some embodiments, the suspension comprises at least about 1 mg or at least about 2 mg chlorpheniramine maleate. In certain embodiments, the suspension comprises at least about 1 mg chlorpheniramine maleate. In other embodiments, the suspension comprise less than or equal to about 5 mg chlorpheniramine maleate.

In some embodiments, the suspension comprises at least about 0.75 mg/mL, at least about 1.00 mg/mL, at least about 1.50 mg/mL, or at least about 2.00 mg/mL chlorpheniramine maleate. In certain embodiments, the suspension comprises about 1.40 mg/mL, about 2.80 mg/mL, or about 7.00 mg/mL chlorpheniramine maleate. In other embodiments, the suspension comprises between about 0.75 mg/mL mg/mL and about 7.00 mg/mL, between about 1.00 mg/mL and about 3.00 mg/mL, between about 2.00 mg/mL and about 3.00 mg/mL, or between about 2.50 mg/mL and about 3.00 mg/mL chlorpheniramine maleate. In certain embodiments, the suspension comprises between about 2.50 mg/mL and about 3.00 mg/mL chlorpheniramine maleate.

In other embodiments in which chlorpheniramine maleate is added as an antihistamine, the suspension comprises at least about 0.15 wt %, at least about 0.17 wt %, at least about 0.20 wt %, or at least about 0.22 wt % chlorpheniramine maleate of the total weight of the suspension. In other embodiments, the suspension comprises between about 0.15 wt % and about 0.30 wt %, between about 0.17 wt % and about 0.25 wt %, or between about 0.20 wt % and about 0.25 wt % chlorpheniramine maleate of the total weight of the suspension. In certain embodiments, the suspension comprises or between about 0.20 wt % and about 0.25 wt % chlorpheniramine maleate of the total weight of the suspension. In yet other embodiments, chlorpheniramine maleate is about 0.22 wt %, about 0.23 wt %, or about 0.24 wt % of the total weight of the suspension.

In some embodiments of the soft gel capsules described herein, wherein the soft gel capsule comprises a suspension as an inner fill and the suspension comprises chlorpheniramine maleate, chlorpheniramine maleate is at least about 0.075 wt %, at least about 0.10 wt %, at least about 0.0125 wt %, or at least about 0.15 wt % of the total weight of the soft gel capsule.

In other embodiments, chlorpheniramine maleate is between about 0.075 wt % and about 0.20 wt %, between about 0.10 wt % and about 0.20 wt %, or between about 0.15 wt % and about 0.20 wt % of the total weight of the soft gel capsule. In certain embodiments, chlorpheniramine maleate is between about 0.10 wt % and about 0.20 wt % or between about 0.15 wt % and about 0.20 wt % of the total weight of the soft gel capsule. In yet other embodiments, chlorpheniramine maleate is about 0.16 wt %, about 0.17 wt %, or about 0.18 wt % of the total weight of the soft gel capsule.

Guaifenesin

As described herein, the suspensions may comprise various combinations of medications suitable for treatment of cold and flu symptoms, including, for example, guaifenesin as an expectorant. In some embodiments, the suspensions of the present disclosure comprise guaifenesin. In some embodiments the suspension comprises about 120 mg, about 200 mg, about 400 mg, or about 600 mg guaifenesin. In certain embodiments the suspension comprises about 200 mg guaifenesin. In some embodiments, the suspension comprises at least about 120 mg or at least about 200 mg guaifenesin. In certain embodiments, the suspension comprises at least about 120 mg guaifenesin. In other embodiments, the suspension comprise less than or equal to about 600 mg or about 400 mg guaifenesin. In some embodiments, the suspension comprises between about 100 mg and about 300 mg guaifenesin.

In some embodiments, the suspension comprises at least about 50 mg/mL, at least about 100 mg/mL, at least about 200 mg/mL, or at least about 250 mg/mL guaifenesin. In certain embodiments, the suspension comprises about 200 mg/mL guaifenesin. In other embodiments, the suspension comprises between about 100 mg/mL and about 800 mg/mL, between about 50 mg/mL and about 500 mg/mL, between about 100 mg/mL and about 300 mg/mL, between about 100 mg/mL and about 500 mg/mL, or between about 100 mg/mL and about 600 mg/mL guaifenesin. In certain embodiments, the suspension comprises between about 100 mg/mL and about 500 mg/mL guaifenesin.

In other embodiments in which guaifenesin is added as an expectorant, the suspension comprises at least about 15 wt %, at least about 16 wt %, at least about 17 wt %, or at least about 17.5 wt % guaifenesin of the total weight of the suspension. In other embodiments, the suspension comprises between about 15 wt % and about 18 wt %, between about 16 wt % and about 18 wt %, or between about 17.5 wt % and about 18.0 wt % guaifenesin of the total weight of the suspension. In certain embodiments, the suspension comprises between about 17.5 wt % and about 18.0 wt % guaifenesin of the total weight of the suspension. In certain other embodiments, the suspension comprises about 17.8 wt % or about 17.9 wt % guaifenesin of the total weight of the suspension.

In some embodiments of the soft gel capsules described herein, wherein the soft gel capsule comprises a suspension as an inner fill and the suspension comprises guaifenesin, guaifenesin is at least about 10 wt %, at least about 11 wt %, at least about 12 wt %, or at least about 13 wt % of the total weight of the soft gel capsule. In yet other embodiments, the suspension comprises about 13.1 wt % or about 13.2 wt % guaifenesin of the total weight of the soft gel capsule.

In other embodiments, guaifenesin is between about 12 wt % and about 14 wt %, between about 12.5 wt % and about 13.5 wt %, or between about 13.0 wt % and about 13.3 wt % of the total weight of the soft gel capsule. In certain embodiments, guaifenesin is between about 13.0 wt % and about 13.3 wt % of the total weight of the soft gel capsule.

Total Active Pharmaceutical Ingredients

Because the present soft gel capsules are intended as combination formulations to treat multiple cold and flu symptoms at the same time, the soft gel capsules and suspensions described herein may be further characterized by the amounts of each active pharmaceutical ingredient all together.

In certain embodiments, the suspension comprises about 325 mg acetaminophen, about 10 mg dextromethorphan HBr, and about 5 mg phenylephrine HCl. In yet other embodiments, the suspension comprises about 325 mg acetaminophen, about 10 mg dextromethorphan HBr, about 5 mg phenylephrine HCl, and about 6.25 mg doxylamine succinate. In still other embodiments, the suspension comprises about 325 mg acetaminophen, about 10 mg dextromethorphan HBr, about 5 mg phenylephrine HCl, and about 2 mg chlorpheniramine maleate. In some embodiments, the suspension comprises about 456 mg/mL acetaminophen, about 14.0 mg/mL dextromethorphan HBr, and about 7.00 mg/mL phenylephrine HCl. In certain embodiments, the suspension comprises about 456 mg/mL acetaminophen, about 14.0 mg/mL dextromethorphan HBr, about 7.00 mg/mL phenylephrine HCl, and about 8.75 mg/mL doxylamine succinate. In other embodiments, the suspension comprises about 456 mg/mL acetaminophen, about 14.0 mg/mL dextromethorphan HBr, about 7.00 mg/mL phenylephrine HCl, and about 2.80 mg/mL chlorpheniramine maleate.

In some embodiments, the suspension comprises about 38.7 wt % acetaminophen, about 1.2 wt % dextromethorphan HBr, and about 0.60 wt % phenylephrine HCl of the total weight of the suspension. In certain embodiments, the suspension comprises about 38.4 wt % acetaminophen, about 1.2 wt % dextromethorphan HBr, about 0.59 wt % phenylephrine HCl, and about 0.74 wt % doxylamine succinate of the total weight of the suspension. In other embodiments, the suspension comprises about 38.6 wt % acetaminophen, about 1.2 wt % dextromethorphan HBr, about 0.59 wt % phenylephrine HCl, and about 0.24 wt % chlorpheniramine maleate of the total weight of the suspension.

In other embodiments, the suspension comprises acetaminophen, dextromethorphan HBr, and phenylephrine HCl, wherein acetaminophen is about 28.8 wt %, dextromethorphan HBr is about 0.88 wt %, and phenylephrine HCl is about 0.44 wt % of the total weight of the soft gel capsule. In certain embodiments, the suspension comprises acetaminophen, dextromethorphan HBr, phenylephrine HCl, and doxylamine succinate, wherein acetaminophen is about 28.9 wt %, dextromethorphan HBr is about 0.89 wt %, phenylephrine HCl is about 0.45 wt %, and doxylamine succinate is about 0.56 wt % of the total weight of the soft gel capsule. In yet other embodiments, the suspension comprises acetaminophen, dextromethorphan HBr, phenylephrine HCl, and chlorpheniramine maleate, wherein acetaminophen is about 27.5 wt %, dextromethorphan HBr is about 0.85 wt %, phenylephrine HCl is about 0.42 wt %, and chlorpheniramine maleate is about 0.17 wt % of the total weight of the soft gel capsule.

Because the active ingredients are used in combination with one another, an alternative way to describe the amounts of each active pharmaceutical ingredient in the suspension is relative to one another as a ratio. In some embodiments, the suspension comprises acetaminophen, dextromethorphan HBr, and phenylephrine HCl in a ratio of 65:2:1. In certain embodiments, the suspension comprises acetaminophen, dextromethorphan HBr, phenylephrine HCl, and doxylamine succinate in a ratio of 65:2:1:1.25. In other embodiments, the suspension comprises acetaminophen, dextromethorphan HBr, phenylephrine HCl, and chlorpheniramine maleate in a ratio of 65:2:1:0.4.

The combined amounts of the active pharmaceutical ingredients may be further described as a collective amount of active ingredients in the suspension. For example, the suspension may comprise acetaminophen, dextromethorphan HBr, phenylephrine HCl, and doxylamine succinate, or alternatively chlorpheniramine maleate, as active pharmaceutical ingredients, and the individual amount of each active contributes to the total quantity of active pharmaceutical ingredients in the suspension. In some embodiments, the suspension comprises a total quantity of active pharmaceutical ingredients of at least about 300 mg, at least about 325 mg, or at least about 340 mg. In other embodiments, the suspension comprises a total quantity of active pharmaceutical ingredients of less than about 750 mg, less than about 500 mg, less than about 450 mg, or less than about 400 mg.

In other embodiments, the suspension comprises about 325 mg acetaminophen, about 10 mg dextromethorphan HBr, and about 5 mg phenylephrine HCl, and about 200 mg guaifenesin. In certain embodiments, the suspension comprises about 342 mg/mL acetaminophen, about 10.5 mg/mL dextromethorphan HBr, about 5.25 mg/mL phenylephrine HCl, and about 210 mg/mL guaifenesin.

In some embodiments, the suspension comprises about 29.0 wt % acetaminophen, about 0.89 wt % dextromethorphan HBr, about 0.45 wt % phenylephrine HCl, and about 17.9 wt % guaifenesin of the total weight of the suspension. In other embodiments, the suspension comprises acetaminophen, dextromethorphan HBr, phenylephrine HCl, and guaifenesin, wherein acetaminophen is about 21.4 wt %, dextromethorphan HBr is about 0.66 wt %, phenylephrine HCl is about 0.33 wt %, and guaifenesin is about 13.2 wt % of the total weight of the soft gel capsule.

In certain embodiments, the suspension comprises acetaminophen, dextromethorphan HBr, phenylephrine HCl, and guaifenesin in a ratio of 65:2:1:40. In certain embodiments wherein the suspension comprises acetaminophen, dextromethorphan HBr, phenylephrine HCl, and guaifenesin, the suspension comprises a total quantity of active pharmaceutical ingredients of at least about 500 mg, at least about 525 mg, or at least about 530 mg. In certain embodiments, the suspension comprises a total quantity of active pharmaceutical ingredients of less than about 750 mg, less than about 600 mg, or less than about 575 mg.

Excipients

As understood in the art, excipients are often present in pharmaceutical formulations as, for example, solubilizing agents, dispersants, and/or crystallization inhibitors, to ensure that the pharmaceutical dosage form remains intact from the processing stage until final use by the consumer. However, it has been found that the use of polyethylene glycol, povidone, and optionally glycerin, in judicious quantities and without further excipients, can stabilize suspensions comprising the above active pharmaceutical ingredients to provide evenly dispersed, high-concentration formulations. The particular selection of polyethylene glycol, povidone, and glycerin as excipients and the judicious control of their quantities are rooted in achieving the proper balance of stability and dispersion of the active pharmaceutical ingredients in the formulation while avoiding excess excipient volume that could otherwise contribute deleteriously to the size of the final soft gel capsule products.

As described above, the soft gel capsule does not contain added water as an excipient in the suspension, which allows for both the stable suspension of active pharmaceutical ingredients in the formulation as well as the reduced size of the soft gel capsule. In other embodiments, the suspension does not contain added water. In yet other embodiments, the suspension is a non-aqueous suspension.

However, although the suspension does not contain added water, an appreciable quantity of adventitious water may migrate into the suspension from the outer shell during encapsulation of and/or drying of the soft gel capsule or over the course of the shelf-life of the capsule. In some embodiments, the suspension comprises less than or equal to 60 mg adventitious water. In some embodiments, the suspension contains less than about 7.0% adventitious water content.

In addition to excluding added water, other common excipients, such as propylene glycol, may also be excluded from the present suspension in order to avoid extraneous material in the inner fill. In some embodiments, the suspension does not contain an alkylene glycol. In certain embodiments, the suspension does not contain propylene glycol.

As described previously, the present inventors have found that the combination of polyethylene glycol and povidone, and optionally glycerin, as excipients is sufficient to provide a stable suspension of active pharmaceutical ingredients for cold and flu medications. The quantities of the excipients in the suspension affect the resulting size of the soft gel capsule but themselves depend upon the quantities of active pharmaceutical ingredients being used. The quantities of the excipients in the suspension can be expressed as an absolute milligram amount (on a per capsule basis). Alternatively, the quantity of the active pharmaceutical ingredients in the suspension may also be represented as a concentration of milligrams per milliliter (mg/mL) of the suspension. As with the active ingredients above, the quantities of the excipients in the suspension may also be expressed as weight percentages of the total weight of the suspension or the total weight of the soft gel capsule.

Polyethylene Glycol

Polyethylene glycol is one of the excipients used in the soft gel capsules described herein to achieve the desired physical properties including, but not limited to, stability the active pharmaceutical ingredients and dispersion of the actives throughout the suspension inner fill. Polyethylene glycol may be identified by other common synonyms known in the art including but not limited to Macrogol and/or PEG.

Particular grades of polyethylene glycol may be especially useful to provide the stable suspensions and even dispersion of the active pharmaceutical ingredients as described herein. Grades of polyethylene glycol may be identified, for example, by weight average molecular weight, degree of polymerization, etc.

In some embodiments, the polyethylene glycol has a weight average molecular weight of at least about 100 g/mol, at least about 200 g/mol, at least about 300 g/mol, at least about 400 g/mol, or at least about 500 g/mol. In certain embodiments, the polyethylene glycol has a weight average molecular weight of at least about 300 g/mol or at least 400 g/mol. In yet other embodiments, the polyethylene glycol has a weight average molecular weight between about 100 g/mol and about 800 g/mol, between about 200 g/mol and about 800 between about 200 g/mol and about 600 g/mol, between about 200 g/mol and about 400 g/mol, between about 300 g/mol and about 700 g/mol, between about 300 g/mol and about 500 g/mol, between about 400 g/mol and about 800 g/mol, between about 400 g/mol and about 600 g/mol, between about 500 g/mol and about 700 g/mol, or between about 600 g/mol and about 800 g/mol. In certain embodiments, the polyethylene glycol has a weight average molecular weight between about 400 g/mol and about 600 g/mol or between about 400 g/mol and about 800 g/mol.

The quantity of polyethylene glycol used as an excipient has a large impact on the resulting properties of the final suspension. In some embodiments, the suspension comprises about 350 mg, about 400 mg, about 450 mg, about 500 mg, about 520 mg, or about 540 mg polyethylene glycol. In certain embodiments, the suspension comprises about 450 mg polyethylene glycol. In other embodiments, the suspension comprises between about 300 mg and about 600 mg, between about 350 mg and about 550 mg, between about 350 mg and about 500 mg, between about 350 mg and about 450 mg, between about 350 mg and about 400 mg, between about 400 mg and about 500 mg, between about 400 mg and about 450 mg, between about 450 mg and about 500 mg, between about 450 mg and about 550 mg, or between about 500 mg and about 550 mg polyethylene glycol. In yet other embodiments, the suspension comprises at least about 350 mg, at least about 400 mg, or at least about 450 mg polyethylene glycol.

In some embodiments, the suspension comprises about 375 mg/mL, about 400 mg/mL, about 450 mg/mL, about 500 mg/mL, about 550 mg/mL, about 600 mg/mL, about 610 mg/mL, about 620 mg/mL, about 630 mg/mL, about 640 mg/mL, about 650 mg/mL, about 660 mg/mL, about 670 mg/mL, about 680 mg/mL, about 690 mg/mL, about 700 mg/mL, about 700 mg/mL, about 750 mg/mL or about 800 mg/mL polyethylene glycol. In certain embodiments, the suspension comprises about 620 mg/mL, about 630 mg/mL, or about 640 mg/mL polyethylene glycol. In other embodiments, the suspension comprises between about 400 mg/mL and about 800 mg/mL, between about 400 mg/mL and about 700 mg/mL, between about 400 mg/mL and about 600 mg/mL, between about 400 mg/mL and about 500 mg/mL, between about 500 mg/mL and about 800 mg/mL, between about 500 mg/mL and about 700 mg/mL, between about 500 mg/mL and about 600 mg/mL, between about 600 mg/mL and about 800 mg/mL, between about 600 mg/mL and about 700 mg/mL, between about 700 mg/mL and about 800 mg/mL, or between about 600 mg/mL and about 650 mg/mL polyethylene glycol. In certain embodiments, the suspension comprises between about 400 mg/mL and about 800 mg/mL, between about 500 mg/mL and about 700 mg/mL, or between about 600 mg/mL and about 650 mg/mL polyethylene glycol.

In other embodiments, the quantity of each excipient can be expressed as a weight percentage of the total weight of the suspension. In some embodiments, the suspension comprises at least about 47.0 wt %, at least about 49.0 wt %, at least about 51.0 wt %, at least about 53.0 wt %, at least about 53.1 w %, at least about 53.2 wt %, at least about 53.3 wt %, at least about 53.4 wt %, at least about 5.35 wt %, or at least about 53.6 wt % polyethylene glycol of the total weight of the suspension. In certain embodiments, the suspension comprises at least about 53.2 wt % or at least about 53.6 wt % polyethylene glycol of the total weight of the suspension. In other embodiments, the suspension comprises between about 47.0 wt % and about 55.0 wt %, between about 47.0 wt % and about 51.0 wt %, between about 53.0 wt % and about 53.8 wt %, between about 53.0 wt % and about 53.4 wt %, between about 53.1 wt % and about 53.7 wt %, between about 53.4 wt % and about 53.8 wt % polyethylene glycol of the total weight of the suspension. In certain embodiments, the suspension comprises between about 53.1 wt % and about 53.7 wt % polyethylene glycol of the total weight of the suspension. In other embodiments, the suspension comprises about 53.2 wt %, about 53.4 wt %, or about 53.6 wt % polyethylene glycol of the total weight of the suspension. In still other embodiments, the suspension comprises about 48.0 wt %, about 48.2 wt %, or about 48.4 wt % polyethylene glycol of the total weight of the suspension.

In some embodiments, polyethylene glycol is at least about 34.0 wt %, at least about 35.0 wt %, at least about 35.5 wt %, at least about 36.0 wt %, at least about 38.0 wt %, at least about 38.5 wt %, at least about 39.0 wt %, at least about 39.5 wt %, or at least about 40.0 wt % of the total weight of the soft gel capsule. In certain embodiments, polyethylene glycol is at least about 35.0 wt %, at least about 38.0 wt %, at least about 39.5 wt % or at least about 40.0 wt % of the total weight of the soft gel capsule. In other embodiments, polyethylene glycol is between about 34.0 wt % and about 40.0 wt %, between about 34.0 wt % and about 36.0 wt %, between about 38.0 wt % and about 40.5 wt %, between about 38.0 wt % and about 40.0 wt %, between about 38.5 wt % and about 40.5 wt %, between about 38.5 wt % and about 40.0 wt %, between about 39.0 wt % and about 40.5 wt %, between about 39.0 wt % and about 40.0 wt %, between about 39.5 wt % and about 40.5 wt %, between about 39.5 wt % and about 40.0 wt %, or between about 40.0 wt % and about 40.5 wt % of the total weight of the soft gel capsule. In certain embodiments, polyethylene glycol is between about 39.5 wt % and about 40.5 wt % of the total weight of the soft gel capsule. In further embodiments, polyethylene glycol is about 38.0 wt %, about 38.5 wt %, about 39.0 wt %, about 39.2 wt %, about 39.4 wt %, about 39.5 wt %, about 39.6 wt %, about 39.8 wt %, about 40.0 wt %, about 40.2 wt %, or about 40.5 wt % of the total weight of the soft gel capsule. In certain embodiments, polyethylene glycol is about 35.5 wt %, about 38.0 wt %, about 39.8 wt % or about 40.0 wt % of the total weight of the soft gel capsule.

It should be recognized that when certain grades of polyethylene glycol are employed, the quantity of the polyethylene glycol may be advantageously chosen based on the properties of that particular grade of PEG to confer the desired properties to the resulting suspension. In certain embodiments, the suspension comprises about 450 mg polyethylene glycol, wherein the polyethylene glycol has a weight average molecular weight of about 400 g/mol.

In certain embodiments, the suspension comprises 53.2 wt % polyethylene glycol of the total weight of the suspension, wherein the polyethylene glycol has a weight average molecular weight of about 400 g/mol. In other embodiments, the suspension comprises 53.6 wt % of the total weight of the suspension, wherein the polyethylene glycol has a weight average molecular weight of about 400 g/mol.

Povidone

Povidone is the other primary excipient employed in the soft gel capsules of the present disclosure as a dispersing agent in the suspension inner fill. Povidone is synonymous with polyvinylpyrrolidone or PVP, but may be referred to by other registered names including Kollidon®.

Different grades of povidone can be utilized as an excipient to achieve the desired physical characteristics of the suspensions of the present disclosure. The grades of povidone may be defined by various attributes known in the art, including weight average molecular weight, viscosity average molecular weight and/or K-value.

In some embodiments of the foregoing, the grade of povidone may be determined by its viscosity, or K-value. In some embodiments, the povidone has an average K-value of between about 11 and about 14. In certain embodiments, the povidone has an average K-value of about 12. In other embodiments, the povidone has an average K-value of between about 28 and about 32. In certain embodiments, the povidone has an average K-value of about 30.

In other embodiments, the grade of povidone may be determined by its weight average molecular weight. In some embodiments, the povidone has a weight average molecular weight of between about 2,000 g/mol and about 3,000 g/mol. In other embodiments, the povidone has a weight average molecular weight of between about 44,000 g/mol and about 54,000 g/mol.

Different quantities of povidone can also be utilized as an excipient to achieve the desired physical characteristics of the suspensions of the present disclosure. In some embodiments, the suspension comprises between about 10 mg and about 75 mg povidone. However, it should be recognized that, similar to polyethylene glycol, the particular grade of povidone used in the suspension may also influence the amount of povidone included in the suspension, depending on the properties of the grade of povidone and the desired properties of the final suspension. For example, in some embodiments, povidone having a lower average K-value may be incorporated into the suspension in greater amounts than povidone having a higher average K-value.

In some embodiments, the suspension comprises about 40 mg, 45 mg, 50 mg, 55 mg or 60 mg povidone, wherein the povidone has an average K-value of between about 11 and about 14. In certain embodiments, the suspension comprises 50 mg povidone. In other embodiments, the suspension comprises at least about 40 mg, at least about 45 mg, at least about 50 mg, or at least about 55 mg povidone, wherein the povidone has an average K-value of between about 11 and about 14. In yet further embodiments, the suspension comprises between about 40 mg and about 60 mg, between about 40 mg and about 55 mg, between about 40 mg and about 50 mg, between about 40 mg and about 45 mg, between about 45 mg and about 60 mg, between about 45 mg and about 55 mg, between about 45 mg and about 50 mg, between about 50 mg and about 60 mg, between about 50 mg and about 55 mg, or between about 55 mg and about 60 mg povidone, wherein the povidone has an average K-value of between about 11 and about 14.

In some embodiments, the suspension comprises at least about 30 mg/mL, at least about 40 mg/mL, at least about 50 mg/mL, at least about 55 mg/mL, at least about 60 mg/mL, at least about 65 g/mL, or at least about 70 mg/mL povidone, wherein the povidone has an average K-value of between about 11 and about 14. In other embodiments, the suspension comprises between about 30 mg/mL and about 90 mg/mL, between about 30 mg/mL and about 70 mg/mL, between about 30 mg/mL and about 50 mg/mL, between about 40 mg/mL and about 70 mg/mL, between about 40 mg/mL and about 60 mg/mL, between about 50 mg/mL and about 90 mg/mL, between about 60 mg/mL and about 80 mg/mL, or between about 65 mg/mL and about 75 mg/mL povidone, wherein the povidone has an average K-value of between about 11 and about 14.

In some embodiments, the suspension comprises at least about 3.50 wt %, at least about 4.00 wt %, at least about 5.00 wt %, at least about 5.20 wt %, at least about 5.50 wt %, at least about 5.75 wt %, at least about 5.80 wt %, at least about 5.85 wt %, at least about 5.90 wt %, or at least about 5.95 wt % povidone of the total weight of the suspension, wherein the povidone has an average K-value of between about 11 and about 14. In other embodiments, the suspension comprises less than 15.0 wt %, less than 10.0 wt %, or less than 7.50 wt % povidone of the total weight of the suspension. In other embodiments, the suspension comprises between about 3.00 wt % and about 15.0 wt %, between about 3.00 wt % and about 5.00 wt %, between about 3.00 wt % and about 4.00 wt %, between about 5.50 wt % and about 6.50 wt %, between about 5.80 wt % and about 6.20 wt %, between about 5.90 wt %, and about 6.10 wt %, or between about 5.80 wt % and about 6.00 wt %, povidone of the total weight of the suspension, wherein the povidone has an average K-value of between about 11 and about 14. In certain embodiments, the suspension comprises about 5.90 wt % or about 5.95 wt % povidone of the total weight of the suspension, wherein the povidone has an average K-value of between about 11 and about 14. In certain other embodiments, the suspension comprises about 3.55 wt % or about 3.60 wt % povidone of the total weight of the suspension, wherein the povidone has an average K-value of between about 11 and about 14.

In some embodiments, povidone is at least about 2.50 wt %, at least about 3.00 wt %, at least about 3.50 wt %, at least about 4.00 wt %, at least about 4.20 wt %, at least about 4.25 wt %, at least about 4.30 wt %, at least about 4.35 wt %, or at least about 4.40 wt %, or at least about 4.45 wt % of the total weight of the soft gel capsule, wherein the povidone has an average K-value of between about 11 and about 14. In certain embodiments, povidone is at least about 4.20 wt %, at least about 4.40 wt % or at least about 4.45 wt % of the total weight of the soft gel capsule. In other embodiments, the suspension comprises less than about 10.0 wt %, less than about 8.00 wt %, less than about 6.00 wt %, or less than about 5.00 wt % povidone of the total weight of the soft gel capsule, wherein the povidone has an average K-value of between about 11 and about 14. In other embodiments, povidone is between about 2.50 wt % and about 5.00 wt %, between about 2.50 wt % and about 4.00 wt %, between about 2.50 wt % and about 3.00 wt %, between about 4.00 wt % and about 5.00 wt %, between about 4.40 wt % and about 4.60 wt %, or between about 4.40 wt % and about 4.50 wt % of the total weight of the soft gel capsule, wherein the povidone has an average K-value of between about 11 and about 14. In certain embodiments, povidone is about 4.42 wt % or about 4.45 wt % of the total weight of the soft gel capsule, wherein the povidone has an average K-value of between about 11 and about 14. In certain other embodiments, povidone is about 2.62 wt % or about 2.63 wt % of the total weight of the soft gel capsule, wherein the povidone has an average K-value of between about 11 and about 14.

In other embodiments, the suspension comprises about 12 mg, about 14 mg, about 16 mg, about 18 mg, about 20 mg, about 22 mg, or about 24 mg povidone, wherein the povidone has an average K-value of between about 28 and about 32. In certain embodiments, the suspension comprises about 18 mg povidone. In still other embodiments, the suspension comprises at least about 12 mg, at least about 14 mg, at least about 16 mg, at least about 18 mg, or at least about 20 mg povidone, wherein the povidone has an average K-value of between about 28 and about 32. In some embodiments, the suspension comprises between about 12 mg and about 24 mg povidone, wherein the povidone has an average K-value of between about 28 and about 32. In some embodiments, the suspension comprises between about 10 mg/mL and about 40 mg/mL, or between about 15 mg/mL and about 35 mg/mL povidone, wherein the povidone has an average K-value of between about 28 and about 32.

In some embodiments, the suspension comprises between about 1.00 wt % and about 2.00 wt % povidone of the total weight of the suspension, wherein the povidone has an average K-value of between about 28 and about 32. In other embodiments, the suspension comprises between about 1.00 wt % and about 2.00 wt % povidone of the total weight of the soft gel capsule, wherein the povidone has an average K-value of between about 28 and about 32.

Excipient Combinations

Although the quantities of polyethylene glycol and povidone may be selected independently of one another, certain combinations of amounts or ratios of PEG and povidone may be especially desirable to provide a stable, high-concentration suspension. For example, in some embodiments, the suspension comprises 450 mg polyethylene glycol and 50 mg povidone. In other embodiments, the suspension comprises polyethylene glycol and povidone in a ratio of 9:1.

The quantities of the excipients should, of course, also be selected with respect to the quantities of the active pharmaceutical ingredients to avoid extraneous amounts of the excipients in the suspension inner fill. As such, there may be ratios of the excipients to the active pharmaceutical ingredients that are highly desirable to provide a stable, evenly dispersed suspension. In some embodiments, the suspension comprises acetaminophen, polyethylene glycol, and povidone in a ratio of 6.5:9:1. In other embodiments, the suspension comprises acetaminophen, polyethylene glycol, and povidone in a ratio of 8.125:13.5:1.

In addition to the above considerations of quantities of the excipients with respect to one another and to the active pharmaceutical ingredients, particular combinations of different grades of polyethylene glycol and povidone or combinations of different grades of the excipients in particular quantities/ratios may also be beneficial to the stability of the resulting suspension. In some embodiments, the suspension comprises polyethylene glycol, wherein the polyethylene glycol has a weight average molecular weight of 400 g/mol, and povidone, wherein the povidone has an average K-value of 12.

Glycerin

In still yet other embodiments, the soft gel capsules of the present invention may further comprise glycerin as an excipient. In some embodiments, the suspension comprises about 40 mg glycerin. In other embodiments, the suspension comprises at least about 20 mg glycerin. In yet further embodiments, the suspension comprises between about 20 and about 50 mg glycerin. In other embodiments, the suspension comprises between about 28 mg/mL and about 70 mg/mL glycerin.

In some embodiments, the suspension comprises between about 2.00 wt % and about 6.00 wt % glycerin of the total weight of the suspension. In other embodiments, the suspension comprises between about 5.00 wt % and about 9.00 wt % glycerin of the total weight of the soft gel capsule.

Additional Suspension Characteristics

The physical properties of active pharmaceutical ingredients and excipients in the suspension will, of course, affect the observed stability of the suspensions, which, as an example, may be characterized by uniformity of dispersion over time. Viscosity of the suspension is one characteristic that could be used to quantitatively assess the stability of the suspension during manufacture. In some embodiments, the inner fill has a viscosity that is between about 2.000 Pa·s and about 4.100 Pa·s. In yet other embodiments, the inner fill has a viscosity that is between about 2.200 Pa·s and about 3.000 Pa·s.

The pH of the suspension is another property of the suspension that may be considered. The acidity or basicity of pharmaceutical combinations is often important for formulation stability both during manufacture and in storage and, is therefore, carefully controlled. However, as described above, the stability of the suspension and reduced size of the soft gel capsule are achieved by the elimination of extraneous ingredients. As such, the suspensions of the present disclosure do not contain any pH modifying ingredients. In some embodiments, the suspension is free of a pH buffering agent. In certain embodiments, the suspension does not contain a pH buffering agent. In other embodiments, the suspension does not contain citric acid or sodium citrate.

Still, the suspension of the present disclosure may be characterized by pH value as the quantities of the active pharmaceutical ingredients and excipients may have their individual pH values and thereby contribute to the pH of the suspension overall. In yet further embodiments, the suspension comprises active pharmaceutical ingredients and excipients and has a pH equal to the intrinsic additive pH of active pharmaceutical ingredients and excipients. In some embodiments, the pH of the suspension is less than about pH 8, less than about pH 7.5, less than about pH 7.0, or less than about pH 6.5. In some embodiments of the foregoing, the pH of the suspension is less than about pH 8. In other embodiments, the pH of the suspension is about pH 6.4. In further embodiments, the pH of the suspension is about pH 6.6. In other embodiments, the pH of the suspension is about pH 6.6. In yet other embodiments, the pH of the suspension is between about pH 6.0 and about pH 8.0, between about pH 6.0 and about pH 7.0, between about pH 6.0 and about pH 6.5, between about pH 6.5 and about pH 7.0, or between about pH 6.2 and about pH 6.8. In certain embodiments, the pH of the suspension is between about pH 6.2 and about pH 6.8.

It should be recognized that the bulk properties of the suspension, including but not limited to viscosity and pH, may be adjusted by altering the quantities and physical properties of the active pharmaceutical ingredients and excipients used herein. For example, the viscosity may be manipulated adjusting the particle size, particle size distribution, and/or volume fraction of solids of active pharmaceutical ingredients.

Outer Shell

As described above, the high-concentration, stable suspension formulation may be encapsulated to provide a soft gel capsule having a fixed but reduced size as an attractive, easy-to-swallow and conveniently portable dosage form for consumers. As is common with liquid-based capsule formulations, the encapsulating material may be a soft outer shell. As such, the present disclosure provides for a soft gel capsule comprising an outer shell encapsulating the inner fill. Also provided are an outer shell and compositions and/or mixtures to be used in the preparation of the outer shell. As understood in the art, a typical outer shell for a soft gel capsule may contain gelatin as the principal encapsulating material, water, and plasticizers such as glycerin and/or sorbitol-sorbitan solution to allow the gelatin to be formed to and retain the desired capsule shape. However, in addition to the gelatin, water, glycerin and/or sorbitol-sorbitan solution of a typical outer shell, the outer shells of the present disclosure may contain one or more further colorants to mask the particles of active pharmaceutical ingredients dispersed in the suspension. With the addition of colorants, such as pearlescent pigments or other opaque materials, the off-putting appearance of suspension can be lessened to provide a soft gel capsule that is stable, reduced in size, and visually appealing to the consumer.

As with and the careful selection of excipients by type and quantity in the high-concentration suspensions above, it is important that the outer shell contain the adequate amounts of each ingredient to have the appropriate encapsulating properties, shelf-stability, and colored appearance without adding undue bulk to the overall soft gel capsule volume. The outer shell components disclosed herein may be quantified, for example, on as milligram amount (per soft gel capsule), as a weight percentage of the total weight of the outer shell mixture or composition, or as a weight percentage of the total weight of a single soft gel capsule.

Gelatin

The soft gel capsules described herein utilize gelatin as the primary matrix for the outer shell, as the physical properties of the gelatin may be readily modified with plasticizers or colorants as needed. In some embodiments, the outer shell comprises gelatin. Certain grades of gelatin, as characterized by, for example, bloom strength, may be utilized in the outer shell. In some embodiments, the outer shell comprises gelatin having a bloom number between about 150 and about 250.

In some embodiments of the foregoing, the outer shell comprises at least about 160 mg, at least about 163 mg, at least about 165 mg, or at least about 169 mg gelatin. In some embodiments, the outer shell comprises between about 160 mg and about 175 mg, between about 160 mg and about 170 mg, between about 160 mg and about 165 mg, between about 165 mg and about 175 mg, or between about 165 mg and about 170 mg gelatin. In yet other embodiments, the outer shell comprises less than about 250 mg, less than about 240 mg, less than about 230 mg, less than about 225 mg, less than about 220 mg, less than about 210 mg, less than about 200 mg, less than about 190 mg, less than 180 mg, less than about 175 mg, or less than 170 mg gelatin. In certain embodiments, the outer shell comprises less than about 175 mg or less than about 170 mg gelatin. In other embodiments, the outer shell comprises less than about 250 mg or less than about 230 mg.

In some embodiments, the outer shell comprises at least about 58.0 wt %, at least about 58.2 wt %, at least about 58.4 wt %, or at least about 58.6 wt % gelatin of the total weight of the outer shell. In certain embodiments, the outer shell comprises at least about 58.3 wt % or at least about 58.7 wt % gelatin of the total weight of the outer shell. In other embodiments, the outer shell comprises less than or equal to about 59.5 wt %, less than or equal to 59.2 wt %, or less than or equal to 59.0 wt %. In other embodiments, the outer shell comprises between about 55.0 wt % and about 60 wt %, between about 59.0 wt % and about 60.0 wt %, between about 58.0 wt % and about 59.0 wt %, between about 58.0 wt % and about 58.5 wt %, or between about 58.5 wt % and about 59.0 wt % gelatin of the total weight of the outer shell. In certain embodiments, the outer shell comprises between about 58.0 wt % and about 59.0 wt %, between about 58.0 wt % and about 58.5 wt %, or between about 58.5 wt % and about 59.0 wt % gelatin of the total weight of the outer shell.

In still further embodiments, gelatin is about 13.0 wt %, about 13.5 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %, about 15.5 wt %, about 15.6 wt %, about 15.7 wt %, about 15.8 wt %, about 16.0 wt %, about 16.5 wt %, about 17.0 wt %, about 17.1 wt %, about 17.2 wt %, about 17.3 wt %, about 17.4 wt %, or about 17.5 wt % of the total weight of the soft gel capsule. In certain embodiments, gelatin is about 14.5 wt % or about 14.9 wt % of the total weight of the soft gel capsule. In other embodiments, gelatin is between about 13.0 wt % and about 18.0 wt %, between about 15.0 wt % and about 18.0 wt %, between about 17.0 wt % and about 18.0 wt %, between about 13.0 wt % and about 16.0 wt %, between about 15.0 wt % and about 16.0 wt %, between about 13.5 wt % and about 15.5 wt %, between about 14.0 wt % and about 15.0 wt %, between about 14.0 wt % and about 14.5 wt %, or between about 14.5 wt % and about 15.0 wt % of the total weight of the soft gel capsule. In certain embodiments, gelatin is between about 14.0 wt % and about 15.0 wt %, between about 14.0 wt % and about 14.5 wt %, or between about 14.5 wt % and about 15.0 wt % of the total weight of the soft gel capsule.

Water

As noted above, the outer shell contains the only added water in the soft gel capsule. Water is added to gelatin to provide a liquid outer shell mixture that is easily manipulated and molded during the manufacturing process. In some embodiments, the outer shell comprises water. In some embodiments, the outer shell comprises between about 20 mg and about 35 mg water. In certain embodiments, the outer shell comprises between about 22.0 mg and about 23.5 mg water, between about 22.1 mg and about 23.4 mg water, between about 22.2 mg and about 23.3 mg water, or between about 22.1 mg and about 23.3 mg water. In certain embodiments, the outer shell comprises between about 22.1 mg and about 23.3 mg water. In yet other embodiments, the outer shell comprises less than about 25.0 mg, less than about 24.5 mg or less than about 23.0 mg water. In other embodiments, the outer shell comprises between about 25.0 mg and about 35.0 mg water, between about 25.0 mg and about 30.0 mg water, between about 26.0 mg and about 28.0 mg water, between about 30 mg and about 35 mg water, or between about 31 mg and about 33 mg water.

The outer shell may also be described as having a particular water content by weight percentage of the total weight of the outer shell or weight percentage of the total weight of the soft gel capsule. In certain embodiments, the outer shell has a water content of about 6 wt %, about 7 wt %, about 8 wt %, about 9 wt %, or about 10 wt % of the total weight of the outer shell. In certain embodiments, the outer shell has a water content of about 6 wt %, about 8 wt %, or about 10 wt % of the total weight of the outer shell. In a further embodiment, the outer shell has a water content of about 8 wt % of the total weight of the outer shell. In other embodiments, the outer shell has a water content between about 6 wt % and about 10 wt % of the total weight of the outer shell. In yet other embodiments, the outer shell has a water content of about 1.0 wt %, about 1.5 wt %, about 2.0 wt %, about 2.1 wt %, about 2.2 wt %, about 2.3 wt %, about 2.4 wt % or about 2.5 wt % of the total weight of the soft gel capsule.

Plasticizers

Plasticizers including, but not limited to, glycerin and sorbitol-sorbitan solution are added to the gelatin in the outer shell to confer the desired material properties of the final outer shell for handling, storage, and use. For example, glycerin and/or sorbitol-sorbitan may be added to increase the plasticity and pliability of the outer shell. In some embodiments, the outer shell comprises one or more plasticizers. In certain embodiments, the one or more plasticizers comprise glycerin. In other embodiments, the one or more plasticizers comprise sorbitol-sorbitan. In yet other embodiments, the outer shell comprises glycerin and sorbitol-sorbitan solution. In certain embodiments, wherein the outer shell comprises glycerin and sorbitol-sorbitan solution, the amount of glycerin and amount of sorbitol-sorbitan solution are the same.

In some embodiments, the outer shell comprises about 40.0 mg, about 41.0 mg, about 42.0 mg, about 42.2 mg, about 42.4 mg, about 42.6 mg, about 42.8 mg, about 43.0 mg, about 43.2 mg, about 43.4 mg, about 43.6 mg, about 43.8 mg, about 44.0 mg, about 44.2 mg, about 44.4 mg, about 44.6 mg, about 44.8 mg, about 45.0 mg, 45.2 mg, about 45.4 mg, about 45.6 mg, about 45.8 mg, about 46.0 mg, about 47.0 mg, about 48.0 mg, about 49.0 mg, about 50.0 mg, about 52 mg, about 54 mg, about 55 mg, about 60 mg, or about 63 mg glycerin. In other embodiments, the outer shell comprises between about 40.0 mg and about 70.0 mg, between about 50.0 mg and about 70.0 mg, between about 40.0 mg and about 60.0 mg, between about 40.0 mg and about 50.0 mg, between about 42.0 mg and about 48.0 mg, or between about 43.0 mg and about 46.0 mg glycerin. In certain embodiments, the outer shell comprises less than about 70 mg or less than about 65 mg glycerin. In yet other embodiments, the outer shell comprises less than about 60.0 mg, less than about 50.0 mg, less than about 49.0 mg, less than about 48.0 mg, less than about 47.0 mg, or less than about 46.0 mg glycerin.

In some embodiments, the outer shell comprises about 40.0 mg, about 41.0 mg, about 42.0 mg, about 42.2 mg, about 42.4 mg, about 42.6 mg, about 42.8 mg, about 43.0 mg, about 43.2 mg, about 43.4 mg, about 43.6 mg, about 43.8 mg, about 44.0 mg, about 44.2 mg, about 44.4 mg, about 44.6 mg, about 44.8 mg, about 45.0 mg, 45.2 mg, about 45.4 mg, about 45.6 mg, about 45.8 mg, about 46.0 mg, about 47.0 mg, about 48.0 mg, about 49.0 mg, about 50.0 mg, about 52 mg, about 54 mg, about 55 mg, about 60 mg, or about 63 mg sorbitol-sorbitan solution. In other embodiments, the outer shell comprises between about 40.0 mg and about 70.0 mg, between about 50.0 mg and about 70.0 mg, between about 40.0 mg and about 60.0 mg, between about 40.0 mg and about 50.0 mg, between about 42.0 mg and about 48.0 mg, or between about 43.0 mg and about 46.0 mg sorbitol-sorbitan solution. In certain embodiments, the outer shell comprises less than about 70 mg or less than about 65 mg sorbitol-sorbitan solution. In yet other embodiments, the outer shell comprises less than about 60.0 mg, less than about 50.0 mg, less than about 49.0 mg, less than about 48.0 mg, less than about 47.0 mg, or less than about 46.0 mg sorbitol-sorbitan solution.

In some embodiments, the outer shell comprises about 13.0 wt %, about 14.0 wt %, about 14.5 wt %, about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.5 wt %, about 17.0 wt %, or about 18.0 wt % glycerin of the total weight of the outer shell. In certain embodiments, the outer shell comprises about 15.6 wt % or about 15.7 wt % of the total weight of the outer shell. In other embodiments, the outer shell comprises between about 13.0 wt % and about 18.0 wt %, between about 14.0 wt % and about 17.0 wt %, between about 15.0 wt % and about 16.0 wt %, between about 15.0 wt % and about 15.7 wt %, or between about 15.3 wt % and about 16.0 wt % glycerin of the total weight of the outer shell. In certain embodiments, the outer shell comprises between about 15.0 wt % and about 16.0 wt %, between about 15.0 wt % and about 15.7 wt %, or between about 15.3 wt % and about 16.0 wt % glycerin of the total weight of the outer shell.

In yet other embodiments, glycerin is about 3.0 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, or about 5.0 wt % of the total weight of the soft gel capsule. In certain embodiments, glycerin is about 3.9 wt %, about 4.0 wt %, about 4.1 wt %, about 4.3 wt %, about 4.5 wt %, or about 4.6 wt % of the total weight of the soft gel capsule. In some embodiments, glycerin is between about 3.0 wt % and about 5.0 wt %, between about 3.7 wt % and about 4.6 wt %, between about 3.5 wt %, and about 4.5 wt %, between about 3.7 wt % and about 4.3 wt %, between about 3.8 wt % and about 4.2 wt %, or between about 3.8 wt % and about 4.1 wt % of the total weight of the soft gel capsule. In certain embodiments, glycerin is between about 3.7 wt % and about 4.3 wt % or between about 3.8 wt % and about 4.1 wt % of the total weight of the soft gel capsule. In other embodiments, glycerin is between about 3.7 wt % and about 4.6 wt % of the total weight of the soft gel capsule.

In some embodiments, the outer shell comprises about 13.0 wt %, about 14.0 wt %, about 14.5 wt %, about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.5 wt %, about 17.0 wt %, or about 18.0 wt % sorbitol-sorbitan solution of the total weight of the outer shell. In certain embodiments, the outer shell comprises about 15.6 wt % or about 15.7 wt % of the total weight of the outer shell. In other embodiments, the outer shell comprises between about 13.0 wt % and about 18.0 wt %, between about 14.0 wt % and about 17.0 wt %, between about 15.0 wt % and about 16.0 wt %, between about 15.0 wt % and about 15.7 wt %, or between about 15.3 wt % and about 16.0 wt % sorbitol-sorbitan solution of the total weight of the outer shell. In certain embodiments, the outer shell comprises between about 15.0 wt % and about 16.0 wt %, between about 15.0 wt % and about 15.7 wt %, or between about 15.3 wt % and about 16.0 wt % sorbitol-sorbitan solution of the total weight of the outer shell.

In yet other embodiments, sorbitol-sorbitan solution is about 3.0 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, or about 5.0 wt % of the total weight of the soft gel capsule. In certain embodiments, sorbitol-sorbitan solution is about 3.9 wt %, about 4.0 wt %, about 4.1 wt %, about 4.3 wt %, about 4.5 wt %, or about 4.6 wt % of the total weight of the soft gel capsule. In some embodiments, sorbitol-sorbitan solution is between about 3.0 wt % and about 5.0 wt %, between about 3.7 wt % and about 4.6 wt %, between about 3.5 wt % and about 4.5 wt %, between about 3.7 wt % and about 4.3 wt %, between about 3.8 wt % and about 4.2 wt %, or between about 3.8 wt % and about 4.1 wt % of the total weight of the soft gel capsule. In certain embodiments, sorbitol-sorbitan solution is between about 3.7 wt % and about 4.3 wt % or between about 3.8 wt % and about 4.1 wt % of the total weight of the soft gel capsule. In other embodiments, sorbitol-sorbitan solution is between about 3.7 wt % and about 4.6 wt % of the total weight of the soft gel capsule.

In still yet other embodiments, the quantities of glycerin and sorbitol-sorbitan solution in the outer shell may be adjusted to provide a total amount of the one or more plasticizers up to about 130 mg per dry capsule, up to about 120 mg per dry capsule, up to about 110 mg per dry capsule, up to about 100 mg per dry capsule or up to about 90 mg per dry capsule. In some embodiments, the outer shell comprises one or more plasticizers, wherein the one or more plasticizers are present at a total amount of between about 90 mg and about 130 mg per dry capsule. It should also be recognized that the individual amounts of each plasticizers in the one or more plasticizers can be varied independently such that the amounts may be identical different. For example, in some embodiments, the outer shell comprises one or more plasticizers, wherein the one or more plasticizers comprise between about 0 mg and about 46 mg sorbitol-sorbitol solution and between about 44 mg and about 90 mg glycerin, and the total amount of the one or more plasticizers is less than or equal to about 90 mg per dry capsule. In some embodiments of the foregoing, the outer shell comprises between about 0.0 wt % and about 5.0 wt % sorbitol-sorbitan solution and between about 3.0 wt % and about 9.0 wt % glycerin of the total weight of the soft gel capsule.

Colorants

Because the particulate matter in the suspension inner fill may detract from the attractiveness of the soft gel capsules, color additives may also be added to the outer shell to improve the visual appeal of the suspension-based soft gel capsule to consumers. In some embodiments, the outer shell comprises one or more colorants. In certain embodiments, the outer shell comprises dyes, pigments and/or colorants. In some embodiments, the outer shell is opaque. In certain embodiments, the outer shell is pearlescent.

In some embodiments, the outer shell comprises dyes. It should be recognized that any food-grade dye known in the art is suitable for use in the outer shell of the present disclosure.

In addition to dyes, other colorant agents may be included to increase the opacity of the outer shell to provide a more attractive appearance to the soft gel capsule. In other embodiments, the outer shell comprises titanium dioxide.

In one embodiment, the outer shell comprises a pearlescent pigment. In certain embodiments, the pearlescent pigment comprises a natural silicate or silica in combination with titanium oxide particles and/or iron oxide particles, wherein the particles have a particle size between about 5 microns and about 150 microns. In certain embodiments, the outer shell comprises a Candurin® pigment. In certain other embodiments, the outer shell comprises a silver or gold pearlescent pigment.

In some embodiments of the foregoing, the outer shell comprises between about 2.0 mg and about 6.0 mg, between about 2.0 mg and about 4.0 mg, between about 3.0 mg and about 6.0 mg, between about 3.0 mg and about 5.0 mg, between about 3.0 mg and about 4.0 mg, between about 4.0 mg and about 6.0 mg, between about 4.0 mg and about 5.0 mg, between about 5.0 mg and about 6.0 mg pearlescent pigment. In certain embodiments, the outer shell comprises between about 3.0 mg and about 6.0 mg, between about 3.0 mg and about 5.0 mg, or between about 4.0 mg and about 6.0 mg pearlescent pigment. In other embodiments, the outer shell comprises about 2.0 mg, about 2.2 mg, about 2.4 mg, about 2.6 mg, about 2.8 mg, about 3.0 mg, about 3.2 mg, about 3.4 mg, about 3.6 mg, about 3.8 mg, about 4.0 mg, about 4.2 mg, about 4.4 mg, about 4.6 mg, about 4.8 mg, about 5.0 mg, about 5.2 mg, about 5.4 mg, about 5.6 mg, about 5.8 mg, or about 6.0 mg pearlescent pigment. In certain embodiments, the outer shell comprises about 3.6 mg or about 5.6 mg pearlescent pigment.

In some embodiments of the foregoing, the outer shell comprises about 0.60 wt %, about 0.65 wt %, about 0.70 wt %, about 0.75 wt %, about 0.80 wt %, about 0.90 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, or about 2.2 wt % pearlescent pigment of the total weight of the outer shell. In certain embodiments, the outer shell comprises about 0.65 wt %, about 0.66 wt %, about 0.70 wt %, about 1.3 wt % or about 2.0 wt % pearlescent pigment of the total weight of the outer shell. In other embodiments, the outer shell comprises between about 0.60 wt % and about 2.2 wt %, between about 0.65 wt % and about 1.0 wt %, between about 0.65 wt % and about 0.70 wt %, between about 1.0 wt % and about 2.2 wt %, between about 1.2 wt % and about 2.1 wt %, between about 1.3 wt % and about 2.0 wt %, between about 1.0 wt % and about 1.5 wt %, between about 1.7 wt % and about 2.2 wt %, or between about 1.2 wt % and about 1.8 wt % of the total weight of the outer shell. In certain embodiments, the outer shell comprises between about 0.65 wt % and about 1.0 wt %, between about 0.65 wt % and about 0.70 wt %, between about 1.0 wt % and about 2.2 wt %, between about 1.2 wt % and about 2.1 wt %, between about 1.0 wt % and about 1.5 wt %, or between about 1.7 wt % and about 2.2 wt % pearlescent pigment of the total weight of the outer shell.

In yet other embodiments, the pearlescent pigment is about 0.15 wt %, about 0.17 wt %, about 0.18 wt %, about 0.19 wt %, about 0.20 wt %, about 0.25 wt %, about 0.30 wt %, about 0.32 wt %, about 0.35 wt %, about 0.37 wt %, about 0.4 wt %, about 0.42 wt %, about 0.45 wt %, about 0.47 wt %, about 0.5 wt %, or about 0.52 wt % of the total weight of the soft gel capsule. In certain embodiments, the pearlescent pigment is about 0.32 wt % or about 0.5 wt % of the total weight of the soft gel capsule. In some embodiments, the pearlescent pigment is between about 0.3 wt % and about 0.5 wt % of the total weight of the soft gel capsule. In other embodiments, the pearlescent pigment is about 0.17 wt % or about 0.18 wt % of the total weight of the soft gel capsule. In some embodiments, the pearlescent pigment is between about 0.15 wt % and about 0.20 wt % of the total weight of the soft gel capsule.

Disintegrants

In addition to the pliability, plasticity, and color of the outer shell used to encapsulate the suspension-based soft gel capsules, it may be desirable to adjust other properties of the outer shell, such as disintegration time to achieve fast-acting relief of symptoms, for improved consumer appeal. The disintegration rate of the soft gel capsules described herein may be adjusted by the introduction of disintegrants and/or superdisintegrants into the outer shell. In still yet other embodiments, the outer shell may further comprise one or more disintegrants and/or superdisintegrants. Disintegrants and superdisintegrants may include, but are not limited to, natural starch, physically and/or chemically modified starch (e.g., sodium starch glycolate), cross-linked polyvinylpyrrolidone, cellulose and derivatives (e.g., microcrystalline cellulose and croscarmellose sodium), and alginates.

Coating

The present disclosure also provides for soft gel capsules comprising an inner fill, an outer shell, and a coating, wherein the outer shell encapsulates the inner fill and the coating is applied to the outer shell. Coatings may be applied to the outer shell of the soft gel capsules as described herein for purposes including, but not limited to, further improvements to aesthetic appearance, flavor modification, ease of ingestion, capsule identification, etc.

In some embodiments, the coating is a film-coating. In other embodiments, the coating is a pharmaceutical glaze. In other embodiments, the coating comprises food-grade shellac.

If it is desired to improve the taste of the soft gel capsule, flavorants and/or sweeteners may be added as a coating to the capsule. In other embodiments, the coating comprises one or more flavorants. In certain embodiments, the coating comprises sugar or an artificial sweetener.

The coating may further include ink for labeling and/or identification. In some embodiments, the coating comprises ink. In certain embodiments, the ink comprises polypropylene glycol.

Methods of Preparing Soft Gel Capsules

As described above, the components of the stable, high-concentration suspension and the colored outer shell are important to provide the final soft gel capsule having a reduced size. Equally as important as the components, however, are the processing conditions used to prepare the high-concentration suspension, the outer shell mixture and the final soft gel capsule. Absent the proper processing conditions, a suspension produced by the active pharmaceutical ingredients and excipients disclosed above may not be stably or evenly mixed. Indeed, even if the proper quantities of the active pharmaceutical ingredients and excipients were to be used to prepare a suspension, the wrong processing conditions could result in soft gel capsules having inconsistent dosage ratios across different batches. The present disclosure provides for methods of preparing suspensions and suspension-based soft gel capsules as described herein.

In one aspect, the present disclosure provides methods of preparing a suspension or a soft gel capsule comprising a suspension, wherein the methods comprise combining the excipients and active pharmaceutical ingredients as described above to provide the suspension. In some embodiments, the methods comprise combining polyethylene glycol, povidone, acetaminophen, dextromethorphan HBr, phenylephrine HCl to provide the suspension. In other embodiments, the methods comprise combining polyethylene glycol, povidone, acetaminophen, dextromethorphan HBr, phenylephrine HCl and optionally an antihistamine, such as doxylamine succinate or chlorpheniramine maleate, to provide the suspension. In still other embodiments, the methods comprise combining polyethylene glycol, povidone, acetaminophen, dextromethorphan HBr, phenylephrine HCl, and guaifenesin to provide the suspension.

Although the active pharmaceutical ingredients and excipients of the suspensions described herein all end up in the final soft gel capsule, the order in which the active pharmaceutical ingredients and excipients are combined may affect the uniformity of the active ingredient dispersion and stability of the resulting suspension. As such, the order of combination for each of the excipients and active pharmaceutical ingredients may be varied to provide the desired suspension characteristics. As one example, excipients may be first combined with one another, and the active pharmaceutical ingredients further admixed individually, at the same time or any combination thereof.

In one aspect, the present disclosure provides a method of preparing a suspension, comprising:
  (a) combining polyethylene glycol and povidone to provide a mixture;
  (b) adding the acetaminophen to the mixture of step (a);
  (c) adding dextromethorphan HBr, phenylephrine HCl, polyethylene glycol, and optionally one or more further active pharmaceutical ingredients to the mixture of step (b) to provide a final mixture;
  (d) heating and stirring the final mixture; and
  (e) cooling the final mixture to provide the suspension.

In some embodiments, the one or more further active ingredients is an antihistamine, an expectorant, or a combination thereof. In certain embodiments, the one or more further active ingredients is selected from the group consisting of doxylamine succinate, chlorpheniramine maleate, and guaifenesin.

For the preparation of a soft gel capsule, the method further includes steps to prepare a colored outer shell mixture and to encapsulate the aforementioned suspension with the outer shell mixture. In another aspect, the present disclosure provides a method of preparing a soft gel capsule, preparing a suspension as described above; preparing an outer shell mixture by combining one or more plasticizers, water, one or more colorants, and gelatin to provide the outer shell mixture; and encapsulating the suspension with the outer shell mixture to provide the soft gel capsule. In certain embodiments of the foregoing, the method of preparing a soft gel capsule comprises:
  (a) combining polyethylene glycol and povidone to provide a mixture;
  (b) adding the acetaminophen to the mixture of step (a);
  (c) adding dextromethorphan HBr, phenylephrine HCl, polyethylene glycol, and optionally one or more further active pharmaceutical ingredients to the mixture of step (b) to provide a final mixture;
  (d) heating and stirring the final mixture;
  (e) cooling the final mixture to provide a suspension as an inner fill;
  (f) combining one or more plasticizers, water, one or more colorants and gelatin to provide an outer shell mixture;
  (g) cooling the outer shell mixture; and
  (h) encapsulating the suspension with the outer shell mixture of step (h) to provide the soft gel capsule.

In some embodiments, the one or more further active ingredients is an antihistamine, an expectorant, or a combination thereof. In certain embodiments, the one or more further active ingredients is selected from the group consisting of doxylamine succinate, chlorpheniramine maleate, and guaifenesin.

To further ensure that the suspensions produced by the present methods are uniformly dispersed, the active pharmaceutical ingredients, excipients, or any mixtures thereof used to prepare the suspensions can be subjected to heat or stirring. In some embodiments, the method comprises pre-heating and stirring one or more of the active pharmaceutical ingredients and/or excipients prior to combining or adding. In other embodiments, the method comprises pre-heating and stirring the one or more plasticizers, water, one or more colorants, or gelatin, or any combinations thereof prior to combining or adding.

Processing Conditions

The processing conditions of the methods and steps as described herein including, but not limited to, temperature, mixing times, and stir rates (rpm) may be especially important to the preparation of a suspension having the desired uniformity, stability and therapeutic efficacy for use in soft gel capsule dosage forms.

For example, the temperature at which the suspension is prepared in the present disclosure may be controlled to produce the desired suspension characteristics. The temperature used for preparing the suspension should be sufficiently high to allow the even mixing of the active ingredients with the excipients but not so high that the active ingredients dissolve in the excipients.

In some embodiments, any one of steps (a), (b), (c), or (d), or any combinations thereof, is performed at a temperature between about 40° C. and about 45° C. In some embodiments, the combining of polyethylene glycol and povidone in step (a) is performed at a temperature between about 40° C. and about 45° C. In other embodiments, the combining of polyethylene glycol and povidone in step (a) is performed at a temperature that is less than about 64° C., less than about 63° C., less than about 62° C., less than about 61° C., or less than about 60° C. In still other embodiments, the adding of acetaminophen to the mixture of step (a) is performed at a temperature between about 40° C. and about 45° C. In yet another embodiment, the adding of acetaminophen to the mixture of step (a) is performed at a temperature that is less than about 64° C., less than about 63° C., less than about 62° C., less than about 61° C., or less than about 60° C.

In some embodiments, the adding of dextromethorphan HBr, phenylephrine HCl, polyethylene glycol, and optionally one or more further active pharmaceutical ingredients, such as doxylamine succinate, chlorpheniramine maleate, or guaifenesin, to the mixture of step (b) to provide a final mixture is performed at a temperature between about 40° C. and about 45° C. In other embodiments, the adding of dextromethorphan HBr, phenylephrine HCl, polyethylene glycol, and optionally one or more further active pharmaceutical ingredients, to the mixture of step (b) to provide a final mixture is performed at a temperature that is less than about 54° C., less than about 53° C., less than about 52° C., less than about 51° C., or less than about 50° C. In further embodiments, the heating and stirring of the final mixture of step (d) is performed at a temperature between about 40° C.

and about 45° C. In still yet other embodiments, the heating and stirring of the final mixture is performed at a temperature that is less than about 54° C., less than about 53° C., less than about 52° C., less than about 51° C., or less than about 50° C.

In some embodiments, the final mixture is cooled to a temperature between about 28° C. and about 32° C. In certain embodiments, the final mixture is cooled to a temperature of about 30° C.

In other embodiments, the combining of one or more plasticizers, water, one or more colorants and gelatin to provide an outer shell mixture in step (f) is performed at a temperature between about 80° C. and about 95° C. In still other embodiments, the outer shell mixture is cooled to a temperature of between about 55° C. and about 65° C. In certain embodiments, the outer shell mixture is cooled to a temperature of about 60° C.

In yet another aspect, the present disclosure provides a method of preparing a suspension, comprising:
(a) combining polyethylene glycol and povidone at a temperature between about 40° C. and about 45° C. to provide a mixture;
(b) adding the acetaminophen to the mixture of step (a) at a temperature between about 40° C. and about 45° C.;
(c) adding dextromethorphan HBr, phenylephrine HCl, polyethylene glycol, and optionally one or more further active pharmaceutical ingredients to the mixture of step (b) at a temperature between about 40° C. and about 45° C. to provide a final mixture;
(d) heating and stirring the final mixture at a temperature between about 40° C. and about 45° C.; and
(e) cooling the final mixture to a temperature of about 30° C.±2° C. to provide the suspension.

In some embodiments, the one or more further active pharmaceutical ingredients is an antihistamine, an expectorant, or a combination thereof. In certain embodiments, the one or more further active pharmaceutical ingredients is selected from the group consisting of doxylamine succinate, chlorpheniramine maleate, and guaifenesin.

In still yet another aspect, the present disclosure provides a method of preparing a soft gel capsule, comprising:
(a) combining polyethylene glycol and povidone at a temperature between about 40° C. and about 45° C. to provide a mixture;
(b) adding the acetaminophen to the mixture of step (a) at a temperature between about 40° C. and about 45° C.;
(c) adding dextromethorphan HBr, phenylephrine HCl, polyethylene glycol, and optionally one or more further active pharmaceutical ingredients to the mixture of step (b) at a temperature between about 40° C. and about 45° C. to provide a final mixture;
(d) heating and stirring the final mixture at a temperature between about 40° C. and about 45° C.;
(e) cooling the final mixture to a temperature between about 28° C. and about 32° C. to provide a suspension as an inner fill;
(f) combining one or more plasticizers, water, one or more colorants and gelatin at a temperature between about 80° C. and about 95° C. to provide an outer shell mixture;
(g) cooling the outer shell mixture to a temperature between about 55° C. and about 65° C.; and
(h) encapsulating the suspension with the outer shell mixture of step (h) to provide the soft gel capsule.

As described herein, any of the steps of the present methods are preferably performed under agitation to ensure uniformity and even distribution of the mixtures and suspensions generated. In some embodiments, agitation includes mixing or stirring. In certain embodiments, the agitation is continuous or intermittent. In other embodiments, the steps of the present methods are performed in one or more reactors capable of agitating the mixtures and suspensions described herein. For example, active ingredients and excipients in the suspension may be combined in, added to, heated in, cooled in, or stored in such a reactor or reactors.

In some embodiments of the present methods, the reactor is a convection mixer. In certain embodiments, the reactor is a low-shear convection mixer. In other embodiments, the reactor is a high-shear convection mixer. In further embodiments, the reactor comprises an anchor mixer or a dispersator. In certain embodiments, the reactor comprises both an anchor mixer and a dispersator. In certain embodiments wherein the reactor comprises both an anchor mixer and a dispersator, the anchor mixer and dispersator may be operated independently of one another or in combination depending on the particular manufacturing step being performed. In some embodiments wherein the reactor comprises an anchor mixer, the mixtures or suspensions described herein are stirred at between about 25 and about 35 rpm. In certain embodiments, the mixtures or suspensions are stirred at about 30 rpm. In other embodiments wherein the reactor comprises a dispersator, the mixtures or suspensions are stirred at between about 1400 and about 1600 rpm. In certain embodiments, the mixtures or suspensions are stirred at about 1500 rpm. In still yet other embodiments, the mixtures or suspensions of the present disclosure are stirred at low-shear, at high-shear, or a combination thereof.

Moreover, the individual active pharmaceutical ingredients, excipients, and/or outer shell components may be agitated prior to combining with other components of the suspension or outer shell mixture, respectively. For example, in some embodiments, the polyethylene glycol and/or the povidone are separately stirred prior to the combining step. In some embodiments, the method of the present disclosure further comprises stirring polyethylene glycol prior to combining the polyethylene glycol with povidone. In other embodiments, the present method comprises stirring povidone prior to combining polyethylene glycol with the povidone. In yet other embodiments, the combining of polyethylene glycol and povidone to provide a mixture in step (a) comprises stirring the mixture.

In still yet other embodiments, the present method comprises stirring the mixture of step (a), comprising polyethylene glycol and povidone, prior to adding acetaminophen to the mixture in step (b). In yet further embodiments, the present method comprises stirring acetaminophen prior to adding the acetaminophen to the mixture in step (b). In still yet other embodiments, the adding of acetaminophen to the mixture in step (b) comprises stirring the mixture after acetaminophen is added.

In some embodiments, the adding of dextromethorphan HBr, phenylephrine HCl, polyethylene glycol, and optionally one or more further active pharmaceutical ingredients, in step (c) comprises adding the dextromethorphan HBr, phenylephrine HCl, and optionally one or more further active pharmaceutical ingredients, such as doxylamine succinate, chlorpheniramine maleate, or guaifenesin, to the mixture of step (b) while stirring and/or dragging with polyethylene glycol to provide a final mixture. In yet another embodiment, cooling of the final mixture in step (f) to provide a suspension comprises stirring the final mixture. In yet other embodiments, the suspension is stirred prior to encapsulation.

Additionally, the period of time over which the individual components of the suspension or outer shell mixture are incorporated with one another during the steps in the present method—i.e., combining/adding, mixing/agitating/stirring, heating, cooling—may be further varied to ensure that the components of the suspension or outer shell mixture are thoroughly combined.

In some embodiments, the polyethylene glycol is stirred for between about 5 min and about 15 min prior to combining with the povidone in step (a). In certain embodiments, the polyethylene glycol is stirred for about 10 min prior to combining with povidone in step (a). In other embodiments, the combining of polyethylene glycol and povidone to provide a mixture in step (a) comprises stirring the mixture for a period of between about 25 minutes and about 35 minutes. In certain embodiments, the combining of polyethylene glycol and povidone to provide a mixture in step (a) comprises stirring the mixture for a period of about 30 minutes.

In some embodiments, the adding acetaminophen to the mixture in step (b) is performed over a period of between about 25 minutes and about 45 minutes or between about 25 minutes and about 60 minutes. In other embodiments, the adding of acetaminophen to the mixture in step (b) comprises stirring the mixture after acetaminophen is added for a period of between about 45 minutes and about 60 minutes. In still other embodiments, the adding of dextromethorphan HBr, phenylephrine HCl, polyethylene glycol, and optionally one or more further active pharmaceutical ingredients, in step (c) is performed over a period of between about 10 minutes and about 15 minutes. In yet other embodiments, the heating and stirring of the final mixture in step (d) is performed for a period of between about 45 minutes and about 60 minutes.

In other embodiments, the cooling of the final mixture to provide a suspension in step (e) is performed over a period of at least about 60 minutes. In yet other embodiments, the suspension is stirred prior to encapsulation for a period of between about 35 minutes and about 45 minutes.

In some embodiments of the present disclosure, the methods and steps described herein are beneficially performed under a controlled atmosphere. In some embodiments, the methods and steps described herein are performed under an inert atmosphere. In other embodiments, the method of preparing a soft gel capsule is performed under nitrogen. In yet other embodiments, the method of preparing a soft gel capsule is performed under vacuum.

In other embodiments, the methods and steps described herein are conducted under controlled light conditions.

In some embodiments of the methods described herein, the active pharmaceutical ingredients may be further selected for or treated to achieve a particular average particle size, a particle size range, or a particle size distribution to facilitate even dispersion.

Additional Processing Steps

The present disclosure further provides additional processing steps to treat any of the mixtures or suspensions as described herein.

In some embodiments of the foregoing methods, the suspension and the outer shell mixture may be sieved to remove large particle impurities prior to cooling. In some embodiments, the final mixture is sieved prior to cooling to provide the suspension. In certain embodiments, the final mixture is sieved through a 1.0 mm mesh prior to cooling to provide the suspension. In some embodiments, the outer shell mixture is sieved prior to cooling. In certain embodiments, the outer shell mixture is sieved through a 0.3 mm mesh, a 0.25 mm mesh, or a combination thereof, prior to cooling.

Provided herein are also processing steps known in the art to prepare soft gel capsules obtained by the methods of the present disclosure for consumer use. For example, after encapsulation and preparation of the suspension-based soft gel capsules, the soft gel capsules may be subjected to drying, visual inspection, sorting, polishing, printing (for labeling), lubrication, and/or bulk packaging.

ENUMERATED EMBODIMENTS

The following enumerated embodiments are representative of some aspects of the present disclosure.

1. A soft gel capsule comprising a suspension, wherein the suspension has a total volume of between 0.50 mL and 0.90 mL and the suspension comprises:
   between 300 mg and 400 mg acetaminophen;
   between 5 mg and 20 mg dextromethorphan HBr,
   between 2.5 mg and 10 mg phenylephrine HCl;
   optionally between 1 mg and 10 mg antihistamine;
   between 400 mg and 500 mg polyethylene glycol; and
   between 25 mg and 75 mg povidone.
2. The soft gel capsule of embodiment 1, wherein the suspension has a total volume of between 0.60 mL and 0.80 mL.
3. The soft gel capsule of embodiment 1 or 2, wherein the suspension comprises 325 mg acetaminophen.
4. The soft gel capsule of any one of embodiments 1 to 3, wherein the suspension comprises 10 mg dextromethorphan HBr.
5. The soft gel capsule of any one of embodiments 1 to 4, wherein the suspension comprises 5 mg phenylephrine HCl.
6. The soft gel capsule of any one of embodiments 1 to 5, wherein the suspension comprises 325 mg acetaminophen, 10 mg dextromethorphan HBr, and 5 mg phenylephrine HCl.
7. The soft gel capsule of any one of embodiments 1 to 6, wherein the antihistamine is doxylamine succinate.
8. The soft gel capsule of embodiment 7, wherein the suspension comprises 6.25 mg doxylamine succinate.
9. The soft gel capsule of any one of embodiments 1 to 6, wherein the antihistamine is chlorpheniramine maleate.
10. The soft gel capsule of embodiment 9, wherein the suspension comprises 2 mg chlorpheniramine maleate.
11. The soft gel capsule of any one of embodiments 1 to 8, wherein the suspension comprises 325 mg acetaminophen, 10 mg dextromethorphan HBr, 5 mg phenylephrine HCl, and 6.25 mg doxylamine succinate.
12. The soft gel capsule of any one of embodiments 1 to 6 or 9 to 10, wherein the suspension comprises 325 mg acetaminophen, 10 mg dextromethorphan HBr, 5 mg phenylephrine HCl, and 2 mg chlorpheniramine maleate.
13. The soft gel capsule of any one of embodiments 1 to 12, wherein the suspension comprises 450 mg polyethylene glycol.
14. The soft gel capsule of any one of embodiments 1 to 13, wherein the polyethylene glycol has a weight average molecular weight of between 400 g/mol and 800 g/mol.
15. The soft gel capsule of any one of embodiments 1 to 14, wherein the polyethylene glycol has a weight average molecular weight of 400 g/mol.
16. The soft gel capsule of any one of embodiments 1 to 15, wherein the suspension comprises 50 mg povidone.
17. The soft gel capsule of any one of embodiments 1 to 16, wherein the povidone has an average K value between 11 and 14.

18. The soft gel capsule of any one of embodiments 1 to 17, wherein the povidone has an average K value of 12.

19. The soft gel capsule of any one of embodiments 1 to 18, wherein the suspension comprises less than or equal to 7.0% adventitious water content.

20. The soft gel capsule of any one of embodiments 1 to 19, wherein the soft gel capsule further comprises an outer shell comprising:
  gelatin;
  purified water;
  one or more plasticizers; and
  one or more colorants.

21. The soft gel capsule of any one of embodiments 1 to 20, wherein the one or more colorants comprises a pearlescent pigment.

22. A soft gel capsule comprising a suspension, wherein the suspension has a total volume of between 0.50 mL and 0.90 mL and the suspension comprises:
  between 300 mg and 400 mg acetaminophen;
  between 5 mg and 20 mg dextromethorphan HBr,
  between 2.5 mg and 10 mg phenylephrine HCl;
  optionally between 1 mg and 10 mg doxylamine succinate;
  between 400 mg and 500 mg polyethylene glycol; and
  between 25 mg and 75 mg povidone.

23. The soft gel capsule of embodiment 22, wherein the suspension has a total volume of between 0.60 mL and 0.80 mL.

24. The soft gel capsule of embodiment 22 or 23, wherein the suspension comprises 325 mg acetaminophen.

25. The soft gel capsule of any one of embodiments 22 to 24, wherein the suspension comprises 10 mg dextromethorphan HBr.

26. The soft gel capsule of any one of embodiments 22 to 25, wherein the suspension comprises 5 mg phenylephrine HCl.

27. The soft gel capsule of any one of embodiments 22 to 26, wherein the suspension comprises 325 mg acetaminophen, 10 mg dextromethorphan HBr, and 5 mg phenylephrine HCl.

28. The soft gel capsule of any one of embodiments 22 to 27, wherein the suspension comprises 6.25 mg doxylamine succinate.

29. The soft gel capsule of any one of embodiments 22 to 28, wherein the suspension comprises 325 mg acetaminophen, 10 mg dextromethorphan HBr, 5 mg phenylephrine HCl, and 6.25 mg doxylamine succinate.

30. The soft gel capsule of any one of embodiments 22 to 29, wherein the suspension comprises 450 mg polyethylene glycol.

31. The soft gel capsule of any one of embodiments 22 to 30, wherein the polyethylene glycol has a weight average molecular weight of between 400 g/mol and 800 g/mol.

32. The soft gel capsule of any one of embodiments 22 to 31, wherein the polyethylene glycol has a weight average molecular weight of 400 g/mol.

33. The soft gel capsule of any one of embodiments 22 to 32, wherein the suspension comprises 50 mg povidone.

34. The soft gel capsule of any one of embodiments 22 to 33, wherein the povidone has an average K value between 11 and 14.

35. The soft gel capsule of any one of embodiments 22 to 34, wherein the povidone has an average K value of 12.

36. The soft gel capsule of any one of embodiments 22 to 35, wherein the suspension comprises less than or equal to 7.0% adventitious water content.

37. The soft gel capsule of any one of embodiments 22 to 36, wherein the soft gel capsule further comprises an outer shell comprising:
  gelatin;
  purified water;
  one or more plasticizers; and
  one or more colorants.

38. The soft gel capsule of any one of embodiments 22 to 37, wherein the one or more colorants comprises a pearlescent pigment.

39. A soft gel capsule comprising a suspension, wherein the suspension has a total volume of between 0.50 mL and 0.90 mL and the suspension comprises:
  between 300 mg and 400 mg acetaminophen;
  between 5 mg and 20 mg dextromethorphan HBr,
  between 2.5 mg and 10 mg phenylephrine HCl;
  optionally between 1 mg and 10 mg chlorpheniramine maleate;
  between 400 mg and 500 mg polyethylene glycol; and
  between 25 mg and 75 mg povidone.

40. The soft gel capsule of embodiment 39, wherein the suspension has a total volume of between 0.60 mL and 0.80 mL.

41. The soft gel capsule of embodiment 39 or 40, wherein the suspension comprises 325 mg acetaminophen.

42. The soft gel capsule of any one of embodiments 39 to 41, wherein the suspension comprises 10 mg dextromethorphan HBr.

43. The soft gel capsule of any one of embodiments 39 to 42, wherein the suspension comprises 5 mg phenylephrine HCl.

44. The soft gel capsule of any one of embodiments 39 to 43, wherein the suspension comprises 325 mg acetaminophen, 10 mg dextromethorphan HBr, and 5 mg phenylephrine HCl.

45. The soft gel capsule of any one of embodiments 39 to 44, wherein the suspension comprises 2 mg chlorpheniramine maleate.

46. The soft gel capsule of any one of embodiments 39 to 45, wherein the suspension comprises 325 mg acetaminophen, 10 mg dextromethorphan HBr, 5 mg phenylephrine HCl, and 2 mg chlorpheniramine maleate.

47. The soft gel capsule of any one of embodiments 39 to 46, wherein the suspension comprises 450 mg polyethylene glycol.

48. The soft gel capsule of any one of embodiments 39 to 47, wherein the polyethylene glycol has a weight average molecular weight of between 400 g/mol and 800 g/mol.

49. The soft gel capsule of any one of embodiments 39 to 48, wherein the polyethylene glycol has a weight average molecular weight of 400 g/mol.

50. The soft gel capsule of any one of embodiments 39 to 49, wherein the suspension comprises 50 mg povidone.

51. The soft gel capsule of any one of embodiments 39 to 50, wherein the povidone has an average K value between 11 and 14.

52. The soft gel capsule of any one of embodiments 39 to 51, wherein the povidone has an average K value of 12.

53. The soft gel capsule of any one of embodiments 39 to 52, wherein the suspension comprises less than or equal to 7.0% adventitious water content.

54. The soft gel capsule of any one of embodiments 39 to 53, wherein the soft gel capsule further comprises an outer shell comprising:
  gelatin;
  purified water;
  one or more plasticizers; and
  one or more colorants.

55. The soft gel capsule of any one of embodiments 39 to 54, wherein the one or more colorants comprises a pearlescent pigment.

56. A soft gel capsule comprising a suspension, wherein the suspension has a total volume of between 0.80 mL and 1.20 mL and the suspension comprises:
  between 300 mg and 400 mg acetaminophen;
  between 5 mg and 20 mg dextromethorphan HBr;
  between 2.5 mg and 10 mg phenylephrine HCl;
  between 100 mg and 300 mg guaifenesin;
  between 450 mg and 550 mg polyethylene glycol; and
  between 40 mg and 60 mg povidone.
57. The soft gel capsule of embodiment 56, wherein the suspension has a total volume of between 0.80 mL and 1.00 mL.
58. The soft gel capsule of embodiment 56 or 57, wherein the suspension comprises 325 mg acetaminophen.
59. The soft gel capsule of any one of embodiments 56 to 58, wherein the suspension comprises 10 mg dextromethorphan HBr.
60. The soft gel capsule of any one of embodiments 56 to 59, wherein the suspension comprises 5 mg phenylephrine HCl.
61. The soft gel capsule of any one of embodiments 56 to 60, wherein the suspension comprises 200 mg guaifenesin.
62. The soft gel capsule of any one of embodiments 56 to 61, wherein the suspension comprises 325 mg acetaminophen, 10 mg dextromethorphan HBr, 5 mg phenylephrine HCl, and 200 mg guaifenesin.
63. The soft gel capsule of any one of embodiments 56 to 62, wherein the suspension comprises 540 mg polyethylene glycol.
64. The soft gel capsule of any one of embodiments 56 to 63, wherein the polyethylene glycol has a weight average molecular weight of between 400 g/mol and 800 g/mol.
65. The soft gel capsule of any one of embodiments 56 to 64, wherein the polyethylene glycol has a weight average molecular weight of 400 g/mol.
66. The soft gel capsule of any one of embodiments 56 to 65, wherein the suspension comprises 40 mg povidone.
67. The soft gel capsule of any one of embodiments 56 to 66, wherein the povidone has an average K value between 11 and 14.
68. The soft gel capsule of any one of embodiments 56 to 67, wherein the povidone has an average K value of 12.
69. The soft gel capsule of any one of embodiments 56 to 68, wherein the suspension comprises less than or equal to 7.0% adventitious water content.
70. The soft gel capsule of any one of embodiments 56 to 69, wherein the soft gel capsule further comprises an outer shell comprising:
  gelatin;
  purified water;
  one or more plasticizers; and
  one or more colorants.
71. The soft gel capsule of any one of embodiments 56 to 70, wherein the one or more colorants comprises a pearlescent pigment.
72. A suspension, comprising:
  at least 400 mg/mL acetaminophen;
  at least 10.0 mg/mL dextromethorphan HBr,
  at least 5.00 mg/mL phenylephrine HCl;
  optionally at least 6.00 mg/mL doxylamine succinate;
  between 500 mg/mL and 700 mg/mL polyethylene glycol; and
  between 60 mg/mL and 80 mg/mL povidone.
73. A suspension, comprising:
  at least 400 mg/mL acetaminophen;
  at least 10.0 mg/mL dextromethorphan HBr;
  at least 5.00 mg/mL phenylephrine HCl;
  optionally at least 1.00 mg/mL chlorpheniramine maleate;
  between 500 mg/mL and 700 mg/mL polyethylene glycol; and
  between 60 mg/mL and 80 mg/mL povidone.
74. The suspension of embodiment 72 or 73, wherein the suspension comprises between 400 mg/mL and 500 mg/mL acetaminophen.
75. The suspension of any one of embodiments 72 to 74, wherein the suspension comprises between 12.0 mg/mL and 16.0 mg/mL dextromethorphan HBr.
76. The suspension of any one of embodiments 72 to 75, wherein the suspension comprises between 6.00 mg/mL and 8.00 mg/mL phenylephrine HCl.
77. The suspension of any one of embodiments 72 to 76, wherein the suspension comprises 456 mg/mL acetaminophen, 14.0 mg/mL dextromethorphan HBr, and 7.00 mg/mL phenylephrine HCl.
78. The suspension of any one of embodiments 72 or 74 to 77, wherein the suspension comprises between 8.00 mg/mL and 9.00 mg/mL doxylamine succinate.
79. The suspension of any one of embodiments 72 or 74 to 78, wherein the suspension comprises 456 mg/mL acetaminophen, 14.0 mg/mL dextromethorphan HBr, 7.00 mg/mL phenylephrine HCl, and 8.75 mg/mL doxylamine succinate.
80. The suspension of any one of embodiments 73 to 77, wherein the suspension comprises between 1.00 mg/mL and 3.00 mg/mL chlorpheniramine maleate.
81. The suspension of any one of embodiments 73 to 78, wherein the suspension comprises 456 mg/mL acetaminophen, 14.0 mg/mL dextromethorphan HBr, 7.00 mg/mL phenylephrine HCl, and 2.80 mg/mL chlorpheniramine maleate.
82. The suspension of any one of embodiments 72 to 81, wherein the suspension comprises between 600 mg/mL and 650 mg/mL polyethylene glycol.
83. The suspension of any one of embodiments 72 to 82, wherein the polyethylene glycol has a weight average molecular weight of between 400 g/mol and 800 g/mol.
84. The suspension of any one of embodiments 72 to 83, wherein the polyethylene glycol has a weight average molecular weight of 400 g/mol.
85. The suspension of any one of embodiments 72 to 84, wherein the suspension comprises between 65 mg/mL and 75 mg/mL povidone.
86. The suspension of any one of embodiments 72 to 85, wherein the povidone has an average K value between 11 and 14.
87. The suspension of any one of embodiments 72 to 86, wherein the povidone has an average K value of 12.
88. The suspension of any one of embodiments 72 to 87, wherein the suspension is non-aqueous.
89. A suspension, comprising:
  at least 250 mg/mL acetaminophen;
  at least 7.00 mg/mL dextromethorphan HBr;
  at least 2.00 mg/mL phenylephrine HCl;
  at least 100 mg/mL guaifenesin;
  between 400 mg/mL and 700 mg/mL polyethylene glycol; and
  between 30 mg/mL and 50 mg/mL povidone.
90. The suspension of embodiment 89, wherein the suspension comprises between 300 mg/mL and 400 mg/mL acetaminophen.
91. The suspension of embodiment 89 or 90, wherein the suspension comprises between 10.00 mg/mL and 15.0 mg/mL dextromethorphan HBr.

92. The suspension of any one of embodiments 89 to 91, wherein the suspension comprises between 5.00 mg/mL and 8.00 mg/mL phenylephrine HCl.

93. The suspension of any one of embodiments 89 to 92, wherein the suspension comprises 342 mg/mL acetaminophen, 10.5 mg/mL dextromethorphan HBr, and 5.25 mg/mL phenylephrine HCl.

94. The suspension of any one of embodiments 89 to 93, wherein the suspension comprises between 100 mg/mL and 300 mg/mL guaifenesin.

95. The suspension of any one of embodiments 89 to 94, wherein the suspension comprises 210 mg/mL guaifenesin.

96. The suspension of any one of embodiments 89 to 95, wherein the suspension comprises 325 mg/mL acetaminophen, 10.0 mg/mL dextromethorphan HBr, 5.00 mg/mL phenylephrine HCl, and 200 mg/mL guaifenesin.

97. The suspension of any one of embodiments 89 to 96, wherein the suspension comprises between 450 mg/mL and 550 mg/mL polyethylene glycol.

98. The suspension of any one of embodiments 89 to 97, wherein the polyethylene glycol has a weight average molecular weight of between 400 g/mol and 800 g/mol.

99. The suspension of any one of embodiments 89 to 98, wherein the polyethylene glycol has a weight average molecular weight of 400 g/mol.

100. The suspension of any one of embodiments 89 to 99, wherein the povidone has an average K value between 11 and 14.

101. The suspension of any one of embodiments 89 to 100, wherein the povidone has an average K value of 12.

102. The suspension of any one of embodiments 89 to 101, wherein the suspension is non-aqueous.

103. A method for preparing a soft gel capsule, comprising:
    (a) combining polyethylene glycol and povidone to provide a mixture;
    (b) adding the acetaminophen to the mixture of step (a);
    (c) adding dextromethorphan HBr, phenylephrine HCl, polyethylene glycol, and optionally one or more further active pharmaceutical ingredients to the mixture of step (b) to provide a final mixture;
    (d) heating and stirring the final mixture;
    (e) cooling the final mixture to provide a suspension as an inner fill;
    (f) combining sorbitol-sorbitan solution, glycerin, water, one or more colorants and gelatin to provide an outer shell mixture;
    (g) cooling the outer shell mixture; and
    (h) encapsulating the suspension with the outer shell mixture of step (h) to provide the soft gel capsule.

104. The method of embodiment 103, wherein the one or more further active pharmaceutical ingredients is an antihistamine, an expectorant, or a combination thereof.

105. The method of embodiment 103 or 104, wherein the one or more further active pharmaceutical ingredients is selected from the group consisting of doxylamine succinate, chlorpheniramine maleate, and guaifenesin.

106. The method of any one of embodiments 103 to 105, wherein any one of steps (a), (b), (c), or (d), or any combinations thereof, are performed at a temperature of between 40° C. and 45° C.

107. The method of any one of embodiments 103 to 106, wherein the final mixture is cooled to a temperature of between 28° C. and 32° C.

108. The method of any one of embodiments 103 to 107, wherein the combining in step (f) is performed at a temperature between about 80° C. and about 95° C.

109. The method of any one of embodiments 103 to 108, wherein the outer shell mixture is cooled to a temperature of between about 55° C. and about 65° C.

110. The method of any one of embodiments 103 to 109, wherein the suspension has a total volume of between 0.50 mL and 1.20 mL.

111. The method of any one of embodiments 103 to 110, wherein the suspension comprises
    between 300 mg and 400 mg acetaminophen;
    between 5 mg and 20 mg dextromethorphan HBr;
    between 2.5 mg and 10 mg phenylephrine HCl.

112. The method of any one of embodiments 103 to 111, wherein the suspension comprises 325 mg acetaminophen, 10 mg dextromethorphan HBr, and 5 mg phenylephrine HCl.

113. The method of any one of embodiments 103 to 112, wherein the suspension comprises 325 mg acetaminophen, 10 mg dextromethorphan HBr, 5 mg phenylephrine HCl, and 6.25 mg doxylamine succinate.

114. The method of any one of embodiments 103 to 112, wherein the suspension comprises 325 mg acetaminophen, 10 mg dextromethorphan HBr, 5 mg phenylephrine HCl, and 2 mg chlorpheniramine maleate.

115. The method of any one of embodiments 103 to 112, wherein the suspension comprises 325 mg acetaminophen, 10 mg dextromethorphan HBr, 5 mg phenylephrine HCl, and 200 mg guaifenesin.

116. The method of any one of embodiments 103 to 114, wherein the soft gel capsule has a total volume of between 0.60 mL and 0.80 mL.

117. The method of embodiments 103 to 111 or 115, wherein the soft gel capsule has a total volume of between 1.00 mL and 1.20 mL.

118. A soft gel capsule prepared according to the method of any one of embodiments 103 to 117.

119. A method for preparing a suspension, comprising:
    (a) combining polyethylene glycol and povidone to provide a mixture;
    (b) adding the acetaminophen to the mixture of step (a);
    (c) adding dextromethorphan HBr, phenylephrine HCl, polyethylene glycol, and optionally one or more further active pharmaceutical ingredients to the mixture of step (b) to provide a final mixture;
    (d) heating and stirring the final mixture; and
    (e) cooling the final mixture to provide the suspension.

120. The method of embodiment 119, wherein the one or more further active pharmaceutical ingredients is an antihistamine, an expectorant, or a combination thereof.

121. The method of embodiment 119 or 120, wherein the one or more further active pharmaceutical ingredients is selected from the group consisting of doxylamine succinate, chlorpheniramine maleate, and guaifenesin.

122. A method for preparing a suspension, comprising:
    (a) combining polyethylene glycol and povidone to provide a mixture;
    (b) adding the acetaminophen to the mixture of step (a);
    (c) adding dextromethorphan HBr, phenylephrine HCl, polyethylene glycol, and optionally doxylamine succinate to the mixture of step (b) to provide a final mixture;
    (d) heating and stirring the final mixture; and
    (e) cooling the final mixture to provide the suspension.

123. The method of embodiment 122, wherein suspension comprises:
    between 400 mg/mL and 500 mg/mL acetaminophen;
    between 12.0 mg/mL and 16.0 mg/mL dextromethorphan HBr;

between 6.00 mg/mL and 8.00 mg/mL phenylephrine HCl;
optionally between 8.00 mg/mL and 9.00 mg/mL doxylamine succinate;
between 500 mg/mL and 700 mg/mL polyethylene glycol; and
between 60 mg/mL and 80 mg/mL povidone.

124. A method for preparing a suspension, comprising:
(a) combining polyethylene glycol and povidone to provide a mixture;
(b) adding the acetaminophen to the mixture of step (a);
(c) adding dextromethorphan HBr, phenylephrine HCl, polyethylene glycol, and chlorpheniramine maleate to the mixture of step (b) to provide a final mixture;
(d) heating and stirring the final mixture; and
(e) cooling the final mixture to provide the suspension.

125. The method of embodiment 124, wherein suspension comprises:
between 400 mg/mL and 500 mg/mL acetaminophen;
between 12.0 mg/mL and 16.0 mg/mL dextromethorphan HBr;
between 6.00 mg/mL and 8.00 mg/mL phenylephrine HCl;
between 1.00 mg/mL and 3.00 mg/mL chlorpheniramine maleate;
between 500 mg/mL and 700 mg/mL polyethylene glycol; and
between 60 mg/mL and 80 mg/mL povidone.

126. A method for preparing a suspension, comprising:
(a) combining polyethylene glycol and povidone to provide a mixture;
(b) adding the acetaminophen to the mixture of step (a);
(c) adding dextromethorphan HBr, phenylephrine HCl, polyethylene glycol, and guaifenesin to the mixture of step (b) to provide a final mixture;
(d) heating and stirring the final mixture; and
(e) cooling the final mixture to provide the suspension.

127. The method of embodiment 126, wherein suspension comprises:
between 300 mg/mL and 400 mg/mL acetaminophen;
between 7.0 mg/mL and 15.0 mg/mL dextromethorphan HBr;
between 2.00 mg/mL and 8.00 mg/mL phenylephrine HCl;
between 100 mg/mL and 300 mg/mL guaifenesin;
between 450 mg/mL and 550 mg/mL polyethylene glycol; and
between 30 mg/mL and 50 mg/mL povidone.

128. The method of any one of embodiments 122 to 127, wherein any one of steps (a), (b), (c), or (d), or any combinations thereof, are performed at a temperature of between 40° C. and 45° C.

129. The method of any one of embodiments 122 to 128, wherein the final mixture is cooled to a temperature of between 28° C. and 32° C.

130. A suspension prepared according to the method of any one of embodiments 122 to 129.

Examples

Example 1: Preparation of Suspension and Suspension-Based Soft Gel Capsule Medication (Suspension Formulations #1 and #2)

In the following example, two suspension-based soft gel capsule medications containing dextromethorphan HBr, acetaminophen, and phenylephrine HCl were prepared. The second of the two suspension-based capsules contained doxylamine succinate as an additional active ingredient designated for nighttime use.

Suspension (Inner Fill) Preparation

Excipients Mixture.

Polyethylene glycol (Macrogol 400) was loaded into a reactor (convection mixer) and stirred (anchor, 30 rpm; dispersator 1500 rpm) for 10±5 min under vacuum (≤−0.7 bar). A portion of total polyethylene glycol was reserved to drag the active pharmaceutical ingredients (APIs) in the second addition step. The polyethylene glycol was heated to 40° C.-45° C. Povidone K12 (Kollidon® 12) is added to the reactor. The polyethylene glycol and povidone were stirred for 30±5 min, under vacuum (≤−0.7 bar), at 40° C.-45° C. Nitrogen gas was introduced into the reactor containing the polyethylene glycol and povidone mixture in order to break vacuum. The mixture was visually assessed for the complete dissolution of povidone into the polyethylene glycol.

$1^{st}$ API Addition.

Acetaminophen was added to the mixture in the reactor over the course of 25-60 minutes, while the mixture was maintained at a temperature of 40° C.-45° C. and continuously stirred (anchor, 30 rpm; dispersator 1500 rpm). Following the complete addition of acetaminophen, the PEG/povidone/acetaminophen mixture was further stirred at the same stir rates for 45-60 minutes at a temperature of 40° C.-45° C., under vacuum (≤−0.7 bar).

Remaining APIs Addition.

Dextromethorphan HBr and phenylephrine HCl (suspension formulation #1) and optionally also doxylamine succinate (suspension formulation #2) were added to the reactor, dragging with the reserved portion of polyethylene glycol (Macrogol 400), over the course of 10-15 minutes, while the reactor mixture was continuously stirred and maintained at a temperature of 40° C.-45° C. The final mixture in the reactor was placed under vacuum (≤−0.7 bar) and stirred for 45-60 minutes at a temperature of 40° C.-45° C.

Cooling and Additional Storage.

After 45-60 minutes, stirring of the final mixture was stopped. The temperature of the final mixture was allowed to cool to 30±2° C. (≥60 minutes). The cooled mixture was sieved through a 1.0 mm mesh to remove large unwanted particles to provide the final high-suspension concentration. After sieving, the suspension was stored in an enclosed tank (30±2° C., under nitrogen gas, under dark conditions) until the encapsulation phase.

FIG. 1 depicts a flow chart corresponding to the preparation of the suspension, as detailed above.

Outer Shell Preparation

Addition of Plasticizers.

Sorbitol solution was added to a reactor, the temperature of which was maintained at 80° C.-95° C. by a reactor jacket. The reactor is placed under vacuum (≤−0.7 bar) and continuously stirred. Glycerin and purified water were added sequentially to the sorbitol solution in the reactor as it was continuously stirred. A portion of the total purified water to be added was reserved to be mixed with the desired colorants.

Addition of Colorants.

The reserved portion of purified water was mixed with the desired colorants (titanium dioxide, FD&C blue #1, D&C Yellow No. 10 and Candurin® Silver Lustre; or D&C Yellow No. 6, FD&C Red #40 and Candurin® Light Gold) for 30 minutes to ensure even dispersion. After 30 minutes, the colorant-water mixture was added to the reactor.

Addition of Gelatin.

Gelatin (Rousselot® 200 AH8, bovine, Rousselot®) was added slowly to the reactor. After ten minutes of gelatin addition, the reactor jacket temperature was increased to 80° C.-95° C. to compensate for the addition of gelatin to avoid formation of lumps. The reactor was placed under vacuum and maintained at a temperature of 80° C.-95° C. as the reactor mixture was continuously stirred until excess purified water was evaporated or approximately 60-120 minutes from the start of deaeration.

Additional purified water was optionally added to the reactor as needed if too much water was evaporated off or if the gelatin did not satisfy visual inspection.

The final outer shell mixture was sieved through a 0.5 mm mesh and a 0.3 mm in series to remove unwanted particles. The sieved mixture was transferred to a storage tank at a temperature of 60±5° C. until the encapsulation phase.

Figure 2:
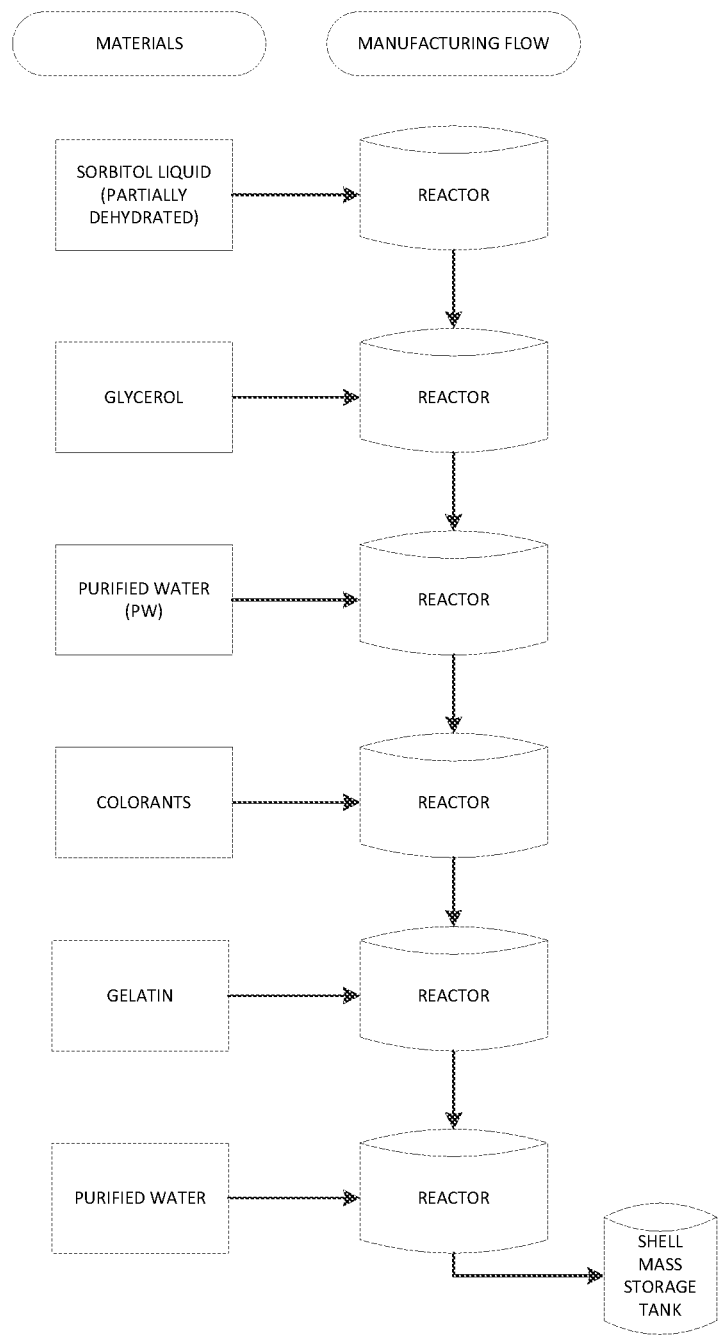
FIG. 2 depicts a process flow chart for preparing an outer shell mixture for use in the soft gel capsules described herein.

FIG. 2 depicts a flow chart corresponding to the preparation of the outer shell mixture, as detailed above.

Soft Gel Capsule Preparation.

Tables 1 and 2 show the target quantities of each ingredient in the suspension-based formulation of the soft gel capsules (in both the inner fill and outer shell on a per dry capsule basis, cps) as compared to formulations for comparative liquid gel capsules prepared in Example 2.

TABLE 1

Comparison of Daytime Formulations: Suspension and Liquid-Gel

| Raw material | Suspension formulation #1 | | Comparative Liquid-gel formulation #3 | |
|---|---|---|---|---|
| | mg/cps | wt % (cps) | mg/cps | wt % (cps) |
| Fill | | | | |
| Dextromethorphan hydrobromide | 10.000 | 0.885 | 10.000 | 0.641 |
| Acetaminophen | 325.000 | 28.762 | 325.000 | 20.832 |
| Phenylephrine hydrochloride | 5.000 | 0.442 | 5.000 | 0.320 |
| Polyethylene Glycol | 450.000 | 39.825 | 595.000 | 38.139 |
| Povidone K12 | 50.000 | 4.425 | 175.000 | 11.217 |
| Propylene Glycol | — | — | 20.000 | 1.282 |
| Purified water | — | — | 30.000 | 1.923 |
| Shell | | | | |
| Gelatin | 169.069 | 14.963 | 239.930 | 15.379 |
| Liquid Sorbitol partially dehydrated | 45.085 | 3.990 | 63.980 | 4.101 |
| Glycerol IPEC | 45.085 | 3.990 | 63.980 | 4.101 |
| D&C Yellow # 6 | 1.879 | 0.166 | 0.118 | 0.008 |
| FD&C Red #40 | — | — | 0.094 | 0.006 |
| Candurin ® Light Gold | 5.636 | 0.499 | — | — |
| Purified water | 23.196 | 2.053 | 32.000 | 2.051 |
| Total | 1,129.95 | 100.00 | 1,560.10 | 100.00 |

TABLE 2

Comparison of Nighttime Formulations: Suspension and Liquid-Gel

| Raw material | Suspension formulation #2 | | Comparative liquid-gel formulation #4 | |
|---|---|---|---|---|
| | mg/cps | wt % (cps) | mg/cps | wt % (cps) |
| Fill | | | | |
| Dextromethorphan hydrobromide | 10.000 | 0.890 | 10.000 | 0.641 |
| Acetaminophen | 325.000 | 28.930 | 325.000 | 20.832 |
| Doxylamine succinate | 6.250 | 0.556 | 6.250 | 0.401 |
| Phenylephrine hydrochloride | 5.000 | 0.445 | 5.000 | 0.320 |
| Polyethylene Glycol | 450.000 | 40.057 | 588.750 | 37.737 |
| Povidone K12 | 50.000 | 4.451 | 175.000 | 11.217 |
| Propylene Glycol | — | — | 20.000 | 1.282 |
| Purified water | — | — | 30.000 | 1.923 |
| Shell | | | | |
| Gelatin | 162.785 | 14.490 | 239.909 | 15.378 |
| Liquid Sorbitol partially dehydrated | 43.409 | 3.864 | 63.976 | 4.101 |
| Glycerol IPEC | 43.409 | 3.864 | 63.976 | 4.101 |
| D&C Yellow no. 10/CFR21 | 0.868 | 0.077 | 0.177 | 0.011 |
| FD&C Blue #1 | 0.543 | 0.048 | 0.088 | 0.006 |
| Titanium dioxide | 0.362 | 0.032 | — | — |
| Candurin ® Silver Lustre | 3.617 | 0.322 | — | — |
| Purified water | 22.157 | 1.972 | 32.000 | 2.051 |
| Total | 1,123.400 | 100.00 | 1,560.13 | 100.00 |

Encapsulation.

During the encapsulation process, the suspension was stirred for 60 seconds every hour to maintain uniform dispersion. The suspension and outer shell mixture were introduced into an encapsulation machine to prepare the final soft gel capsules, with the machine parameters set as indicated in Table 3 below.

Post-Encapsulation Processing.

Figure 3:
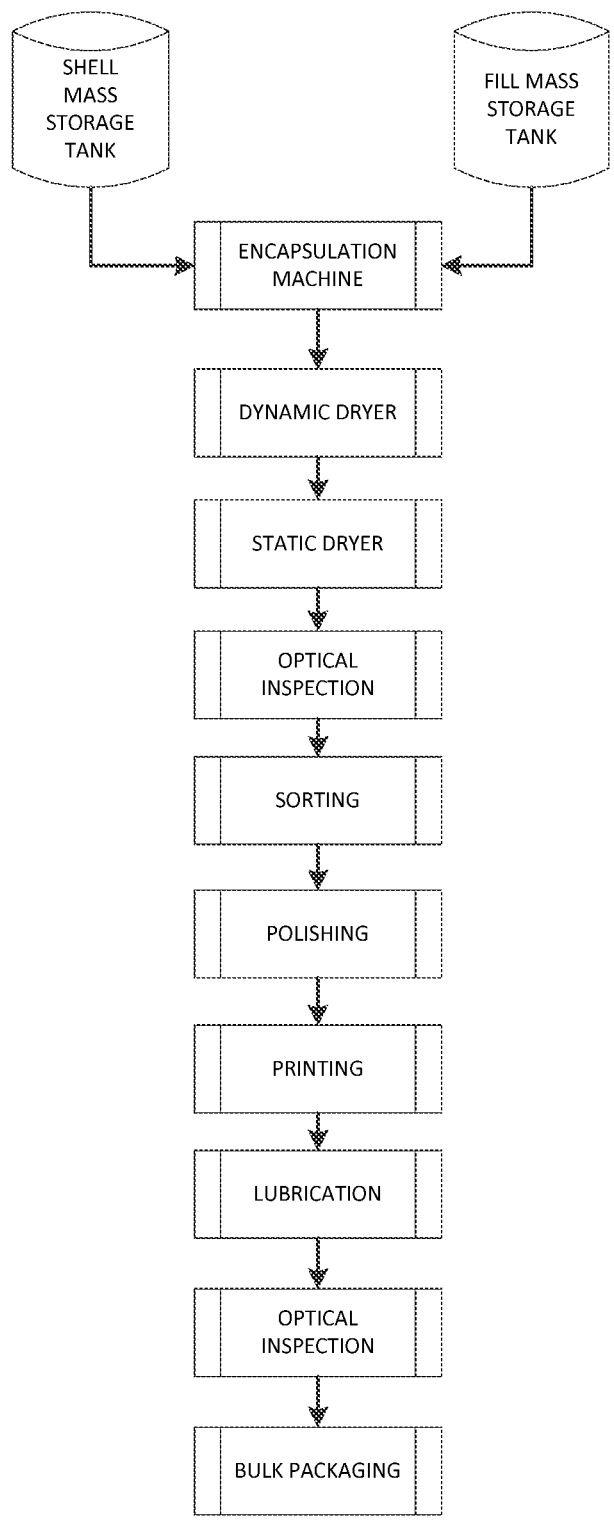
FIG. 3 depicts a process flow chart for preparing soft gel capsules for packaging after encapsulation.

After encapsulation, the soft gel capsules were further processed according to standard methods in the art, as shown in FIG. 3, prior to packaging.

TABLE 3

Encapsulation Parameters

| Parameter | Setting |
| --- | --- |
| Mean fill weight (with doxylamine) | Target: (846.25 + 3.7%) mg/capsule = 877.6 mg/cap |
| Mean fill weight (without doxylamine) | Target: (840 + 3.7%) mg/capsule = 871.1 mg/cap |
| Ribbon thickness | 0.035-0.039 in |
| Seam thickness | ≥0.012 in (for individual values) |

Example 2: Preparation of Liquid Gel Formulation and Liquid-Gel Capsule Medication (Liquid-Gel Formulations #3 and #4)

The following example describes the preparation of two liquid gel formulations containing dextromethorphan HBr, acetaminophen, phenylephrine HCl, and optionally doxylamine succinate, as well as the preparation of liquid-gel capsules containing the formulations.

Liquid Inner Fill Preparation

Excipients Mixture.

Polyethylene glycol (Macrogol 400), propylene glycol, and purified water were loaded into a reactor (convection mixer) and stirred (anchor, 30 rpm; dispersator 1500 rpm) for at least 15 min under nitrogen atmosphere at room temperature. A portion of total polyethylene glycol was reserved to be dragged with the active pharmaceutical ingredients (APIs) in the second addition step. Povidone K12 (Kollidon® 12) was added to the reactor. The reactor was heated to 40° C.-45° C., and the mixture in the reactor was stirred under vacuum for at least 30 minutes. After at least 30 minutes, the reactor was back-filled with nitrogen to allow for visual inspection of the povidone into the mixture.

Stirring with the dispersator was stopped and the temperature of the reactor was increased to about 65° C. (64° C.-68° C.) to prepare for the addition of acetaminophen.

1$^{st}$ API Addition.

Acetaminophen was slowly added to the above mixture in the reactor over the course of ≤1 h 15 min, while the mixture was maintained at a temperature of 64° C.-68° C. and continuously stirred (1$^{st}$ third of the addition with anchor, 25 rpm; and for the remaining two thirds of the addition with dispersator 1500 rpm). Following the complete addition of acetaminophen, the PEG/povidone/acetaminophen mixture was further stirred at the same stir rates for 60 minutes at a temperature of 64° C.-68° C., under nitrogen. The mixture was evaluated visually for the complete dissolution of acetaminophen prior to further addition of the remaining APIs.

Remaining APIs Addition.

The reactor temperature was reduced to 54° C.-57° C. for the addition of the remaining active ingredients. Dextromethorphan HBr and phenylephrine HCl (comparative liquid gel formulation #3), and optional also doxylamine succinate (comparative liquid gel formulation #4), were added to the reactor, dragging with the reserved polyethylene glycol. The final mixture in the reactor was placed under nitrogen and stirred for 30-60 minutes at a temperature of 54° C.-57° C. The final mixture was visually assessed to ensure complete dissolution of the remaining APIs.

Cooling and Additional Storage.

After 30-60 Minutes, Stirring of the Final Mixture was stopped. The temperature of the final mixture was allowed to cool to 30° C.-35° C. by lowering the temperature of the reactor jacket over the course of at least 60 minutes. Once the temperature had cooled to below 45° C., the reactor was placed under vacuum. The final mixture was continuously stirred throughout the cooling process. The cooled mixture was sieved through a 0.3 mm mesh, followed by a 0.25 mm mesh to remove large unwanted particles to provide the final liquid gel formulation. After sieving, the liquid formulation was stored in an enclosed tank (30±2° C., under nitrogen gas, under dark conditions) until the encapsulation phase.

Figure 4:
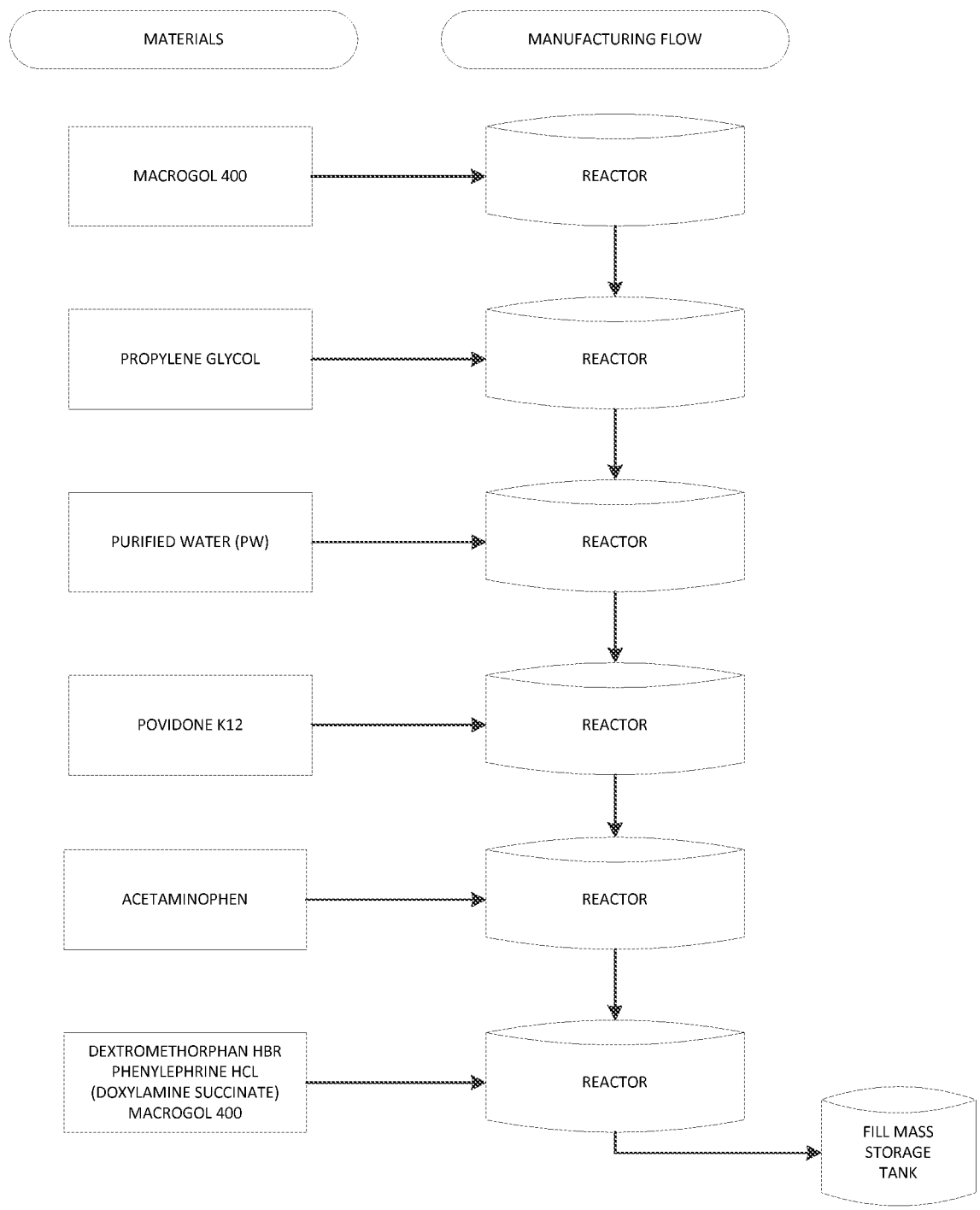
FIG. 4 depicts a process flow chart for preparing solution-based liquid-gel cold and flu formulations.

FIG. 4 depicts a flow chart corresponding to the preparation of the liquid inner fill formulation, as detailed above.

Outer Shell Preparation

Addition of Plasticizers.

Sorbitol solution was added to a reactor, the temperature of which was maintained at 80° C.-92° C. by a reactor jacket. The reactor was placed under vacuum (≤−0.7 bar) and continuously stirred. Glycerin and purified water were added sequentially to the sorbitol solution in the reactor as it was continuously stirred. A portion of the total purified water to be added was reserved to be mixed with the desired colorants.

Addition of Gelatin.

After ten minutes of glycerol addition, gelatin (Rousselot® 200 AH8, bovine, Rousselot®) was added slowly to the reactor to avoid formation of lumps. The reactor jacket temperature was maintained at 80° C.-92° C. to compensate for the addition of gelatin.

Addition of Colorants.

The reserved portion of purified water was mixed with the desired colorants (FD&C blue #1 and D&C Yellow No. 10; or D&C Yellow No. 6 and FD&C Red #40) for 30 minutes to ensure even dispersion. After 30 minutes, the colorant-water mixture was added to the reactor.

The reactor was placed under vacuum as the reactor mixture was continuously stirred until excess purified water was evaporated or approximately 60-120 minutes from the start of deaeration.

Additional purified water was optionally added to the reactor as needed if too much water was evaporated off or if the gelatin did not satisfy visual inspection.

The final outer shell mixture was sieved through a 0.5 mm mesh and a 0.3 mm in series to remove unwanted particles.

The sieved mixture was transferred to a storage tank at a temperature of 62±5° C. until the encapsulation phase.

Soft Gel Capsule Preparation.

Tables 1 and 2 show the target quantities of each ingredient in the liquid-based formulation of the soft gel capsules (in both the inner fill and outer shell on a per capsule basis) as compared to suspension-based soft gel capsules in Example 1.

Encapsulation.

The suspension and outer shell mixture were introduced into an encapsulation machine to prepare the final soft gel capsules, with the machine parameters set as indicated in Table 4 below.

Post-Encapsulation Processing.

After encapsulation, the soft gel capsules were further processed according to standard methods in the art, as shown in FIG. 3, prior to packaging.

TABLE 4

Encapsulation Parameters

| Parameter | Setting |
| --- | --- |
| Mean fill weight | Target: (1160.0 + 3.4%) mg/capsule = 1999.4 mg/cap |
| Ribbon thickness | 0.033-0.035 in. |
| Seam thickness | ≥0.007 in (for individual values) |

Example 3: Preparation of Suspension and Suspension-Based Soft Gel Capsule Medication (Suspension Formulation #5)

In the example below, a suspension-based soft gel capsule medication containing dextromethorphan HBr, acetaminophen, phenylephrine HCl, and chlorpheniramine maleate was prepared.

Suspension (Inner Fill) Preparation

Excipients Mixture.

Polyethylene glycol (Macrogol 400) was loaded into a reactor (convection mixer) and stirred (anchor, 30 rpm; dispersator 1500 rpm) for 10±5 min under vacuum (≤−0.7 bar). A portion of total polyethylene glycol was reserved to drag the active pharmaceutical ingredients (APIs) in the second addition step. The polyethylene glycol was heated to 40° C.-45° C. Povidone K12 (Kollidon® 12) was added to the reactor.

The polyethylene glycol and povidone were stirred for 30±5 min, under vacuum (≤−0.7 bar), at 40° C.-45° C. Nitrogen gas was introduced into the reactor containing the polyethylene glycol and povidone mixture in order to break vacuum. The mixture was visually assessed for the complete dissolution of povidone into the polyethylene glycol.

1st API Addition.

Acetaminophen was added to the mixture in the reactor over the course of 25-60 minutes, while the mixture was maintained at a temperature of 40° C.-45° C. and continuously stirred (anchor, 30 rpm; dispersator 1500 rpm). Following the complete addition of acetaminophen, the PEG/povidone/acetaminophen mixture was further stirred at the same stir rates for 45-60 minutes at a temperature of 40° C.-45° C., under vacuum (≤−0.7 bar).

Remaining APIs Addition.

Dextromethorphan HBr, phenylephrine HCl and chlorpheniramine maleate were added to the reactor, dragging with the reserved portion of polyethylene glycol (Macrogol 400), over the course of 10-15 minutes, while the reactor mixture was continuously stirred and maintained at a temperature of 40° C.-45° C. The final mixture in the reactor was placed under vacuum (≤−0.7 bar) and stirred for 45-60 minutes at a temperature of 40° C.-45° C.

Cooling and additional storage. After 45-60 minutes, stirring of the final mixture was stopped. The temperature of the final mixture was allowed to cool to 30±2° C. (≥60 minutes). The cooled mixture was sieved through a 1.0 mm mesh to remove large unwanted particles to provide the final high-suspension concentration. After sieving, the suspension was stored in an enclosed tank (30±2° C., under nitrogen gas, under dark conditions) until the encapsulation phase.

Figure 5:
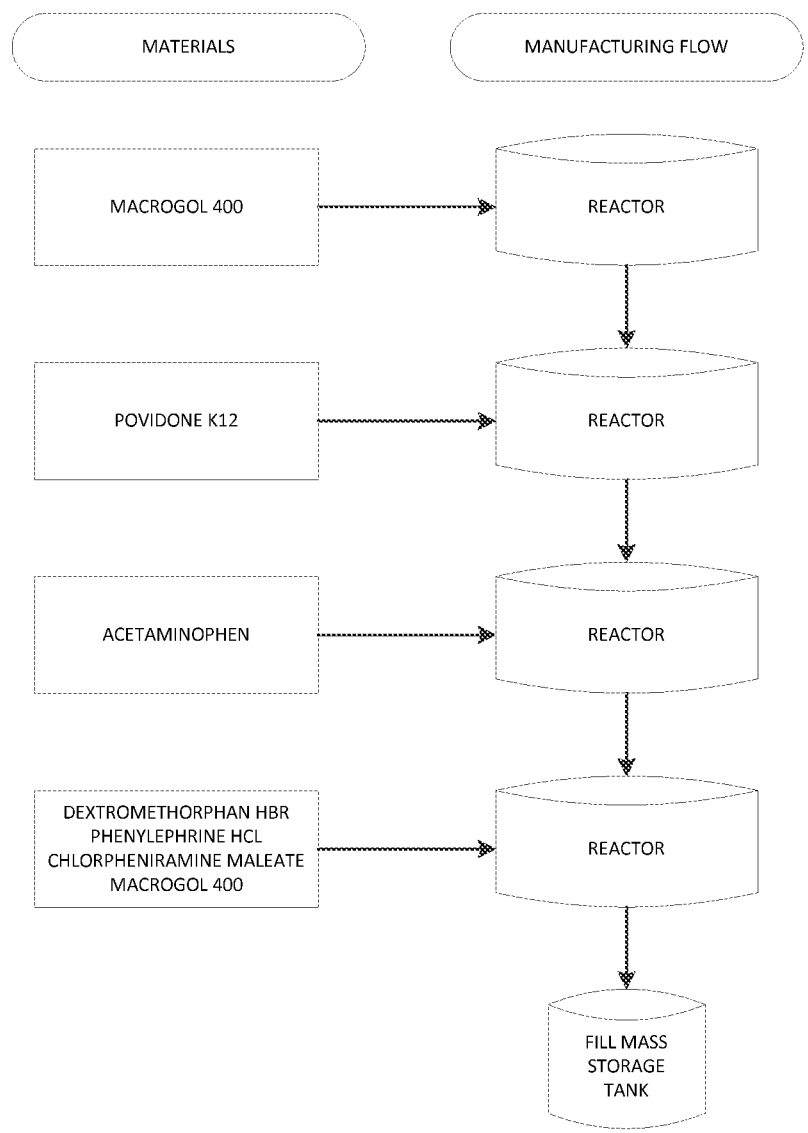
FIG. 5 depicts a process flow chart for preparing a suspension-based cold and flu formulation containing acetaminophen, dextromethorphan HBr, phenylephrine HCl, and chlorpheniramine maleate.

FIG. 5 depicts a flow chart corresponding to the preparation of the suspension, as detailed above.

Outer Shell Preparation

Addition of Plasticizers.

Sorbitol solution was added to a reactor, the temperature of which was maintained at 80° C.-95° C. by a reactor jacket. The reactor was placed under vacuum (≤−0.7 bar) and continuously stirred. Glycerin and purified water were added sequentially to the sorbitol solution in the reactor as it was continuously stirred. A portion of the total purified water to be added was reserved to be mixed with the desired colorants.

Addition of Colorants.

The reserved portion of purified water was mixed with the desired colorants (D&C Red No 33/CFR 21, FD&C blue #1 and Candurin® Silver for 30 minutes to ensure even dispersion. After 30 minutes, the colorant-water mixture was added to the reactor.

Addition of Gelatin.

Gelatin (bovine origin, Rousselot® 200 AH8 or Gelatin 180 BLOOM BLH-GELITA®) was added slowly to the reactor. After ten minutes of gelatin addition, the reactor jacket temperature was increased to 80° C.-95° C. to compensate for the addition of gelatin to avoid formation of lumps.

The reactor was placed under vacuum and maintained at a temperature of 80° C.-95° C. as the reactor mixture was continuously stirred until excess purified water was evaporated or approximately 60-120 minutes from the start of deaeration.

Additional purified water was optionally added to the reactor as needed if too much water was evaporated off or if the gelatin did not satisfy visual inspection.

The final outer shell mixture was sieved through a 0.5 mm mesh and a 0.3 mm in series to remove unwanted particles. The sieved mixture was transferred to a storage tank at a temperature of 60±5° C. until the encapsulation phase.

FIG. 2 depicts a flow chart corresponding to the preparation of the outer shell mixture, as detailed above.

Soft Gel Capsule Preparation.

Table 5 shows the target quantities of each ingredient in the suspension-based formulation of the soft gel capsules (in both the inner fill and outer shell on a per dry capsule basis, cps) as compared to a formulation for a comparative liquid gel capsule. The comparative liquid gel capsule was prepared according to the method in Example 2, substituting doxylamine succinate with chlorpheniramine maleate.

TABLE 5

Comparison of Suspension-Based Capsule and Liquid-Gel Capsule Formulations

| Raw material | Suspension formulation #5 | | Comparative liquid-gel formulation #6 | |
|---|---|---|---|---|
| | mg/cps | wt % (cps) | mg/cps | wt % (cps) |
| Fill | | | | |
| Dextromethorphan hydrobromide | 10.000 | 0.846 | 10.000 | 0.643 |
| Acetaminophen | 325.000 | 27.496 | 325.000 | 20.890 |
| Phenylephrine hydrochloride | 5.000 | 0.423 | 5.000 | 0.321 |
| Chlorpheniramine maleate | 2.000 | 0.169 | 2.000 | 0.129 |
| Polyethylene Glycol | 450.000 | 38.071 | 588.750 | 37.843 |
| Povidone K12 | 50.000 | 4.230 | 175.000 | 11.249 |
| Propylene Glycol | — | — | 20.000 | 1.286 |
| Purified water | — | — | 30.000 | 1.928 |
| Shell | | | | |
| Gelatin | 202.281 | 17.113 | 239.868 | 15.418 |
| Liquid Sorbitol partially dehydrated | 53.941 | 4.564 | 63.965 | 4.112 |
| Glycerol IPEC | 53.941 | 4.564 | 63.965 | 4.112 |
| D&C Red No. 33/CFR 21 | 0.382 | 0.032 | 0.1274 | 0.008 |
| FD&C Blue # 1 | 0.007 | 0.001 | 0.0746 | 0.005 |
| Candurin ® Silver Lustre | 2.248 | 0.190 | — | — |
| Purified water | 27.200 | 2.301 | 32.000 | 2.057 |
| Total | 1,182.000 | 100.000 | 1,555.750 | 100.00 |

Encapsulation.

During the encapsulation process, the suspension was stirred for 60 seconds every hour to maintain uniform dispersion. The suspension and outer shell mixture were introduced into an encapsulation machine to prepare the final soft gel capsules, with the machine parameters set as indicated in Table 6 below.

Post-Encapsulation Processing.

After encapsulation, the soft gel capsules were further processed according to standard methods in the art, as shown in FIG. 3, prior to packaging.

TABLE 6

Encapsulation Parameters

| Parameter | Setting |
|---|---|
| Mean fill weight (with chlorpheniramine maleate) | Target: (842.0 + 3.7%) mg/cps = 873.2 mg/cps |
| Ribbon thickness | 0.035-0.039 in |
| Seam thickness | ≥0.012 in (for individual values) |

Example 4: Preparation of Suspension and Suspension-Based Soft Gel Capsule Medication (Suspension Formulation #7)

The example below describes the preparation of a suspension-based soft gel capsule medication containing guaifenesin, dextromethorphan HBr, acetaminophen, and phenylephrine HCl.

Suspension (Inner Fill) Preparation
  Excipients Mixture.

Polyethylene glycol (Macrogol 400) was loaded into a reactor (convection mixer) and stirred (anchor, 30 rpm; dispersator 1500 rpm) for 10±5 min under vacuum (≤−0.7 bar). A portion of total polyethylene glycol was reserved to drag the active pharmaceutical ingredients (APIs) in the second addition step. The polyethylene glycol was heated to 40° C.-45° C. Povidone K12 (Kollidon® 12) was added to the reactor.

The polyethylene glycol and povidone were stirred for 30±5 min, under vacuum (≤−0.7 bar), at 40° C.-45° C. Nitrogen gas was introduced into the reactor containing the polyethylene glycol and povidone mixture in order to break vacuum. The mixture was visually assessed for the complete dissolution of povidone into the polyethylene glycol.

1$^{st}$ API Addition.

Acetaminophen was added to the mixture in the reactor over the course of 25-60 minutes, while the mixture was maintained at a temperature of 40° C.-45° C. and continuously stirred (anchor, 30 rpm; dispersator 1500 rpm). Following the complete addition of acetaminophen, the PEG/povidone/acetaminophen mixture was further stirred at the same stir rates for 45-60 minutes at a temperature of 40° C.-45° C., under vacuum (≤−0.7 bar).

Remaining APIs Addition.

Guaifenesin, dextromethorphan HBr and phenylephrine HCl were added to the reactor, dragging with the reserved portion of polyethylene glycol (Macrogol 400), over the course of 25-60 minutes, while the reactor mixture was continuously stirred and maintained at a temperature of 40° C.-45° C. The final mixture in the reactor was placed under vacuum (≤−0.7 bar) and stirred for 45-60 minutes at a temperature of 40° C.-45° C.

Cooling and Additional Storage.

After 45-60 minutes, stirring of the final mixture was stopped. The temperature of the final mixture was allowed to cool to 30±2° C. (≥60 minutes). The cooled mixture was sieved through a 1.0 mm mesh to remove large unwanted particles to provide the final high-suspension concentration. After sieving, the suspension was stored in an enclosed tank (30±2° C., under nitrogen gas, under dark conditions) until the encapsulation phase.

Figure 6:
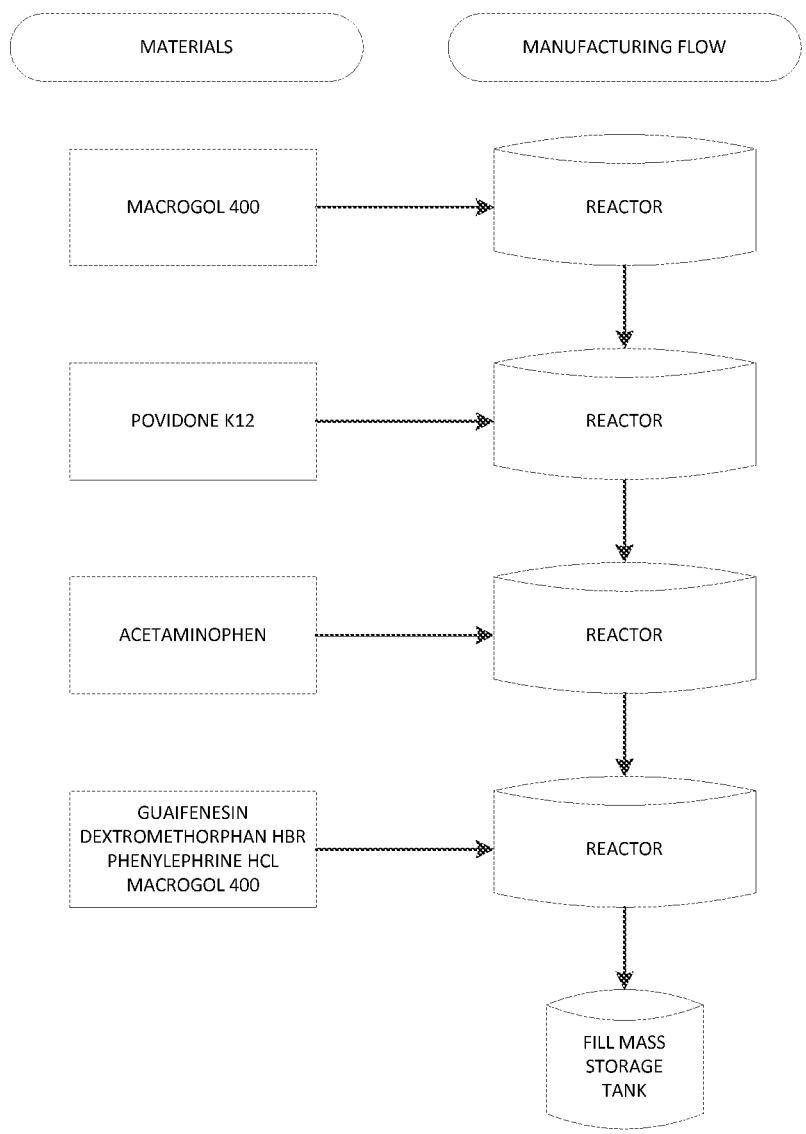
FIG. 6 depicts a process flow chart for preparing a suspension-based cold and flu formulation containing acetaminophen, dextromethorphan HBr, phenylephrine HCl, and guaifenesin.

FIG. 6 depicts a flow chart corresponding to the preparation of the suspension, as detailed above.

Outer Shell Preparation
  Addition of Plasticizers.

Sorbitol solution was added to a reactor, the temperature of which was maintained at 80° C.-95° C. by a reactor jacket. The reactor was placed under vacuum (≤−0.7 bar) and continuously stirred. Glycerin and purified water were added sequentially to the sorbitol solution in the reactor as it was continuously stirred. A portion of the total purified water to be added was reserved to be mixed with the desired colorants.

Addition of Colorants.

The reserved portion of purified water was mixed with the desired colorants FD&C Red #40 and Candurin® Silver for 30 minutes to ensure even dispersion. After 30 minutes, the colorant-water mixture was added to the reactor.

Addition of Gelatin.

Gelatin (bovine origin, Rousselot® 200 H8 or Gelatin 180 BLOOM GELITA®) was added slowly to the reactor. After ten minutes of gelatin addition, the reactor jacket temperature was increased to 80° C.-95° C. to compensate for the addition of gelatin to avoid formation of lumps.

The reactor was placed under vacuum and maintained at a temperature of 80° C.-95° C. as the reactor mixture was continuously stirred until excess purified water was evaporated or approximately 60-120 minutes from the start of deaeration.

Additional purified water was optionally added to the reactor as needed if too much water was evaporated off or if the gelatin did not satisfy visual inspection.

The final outer shell mixture was sieved through a 0.5 mm mesh and a 0.3 mm in series to remove unwanted particles.

The sieved mixture was transferred to a storage tank at a temperature of 60±5° C. until the encapsulation phase.

FIG. 2 depicts a flow chart corresponding to the preparation of the outer shell mixture, as detailed above.

Soft Gel Capsule Preparation.

Table 7 shows the target quantities of each ingredient in the suspension-based formulation of the soft gel capsules (in both the inner fill and outer shell on a per dry capsule basis, cps).

TABLE 7

| Raw material | Suspension formulation # 7 | |
|---|---|---|
| | mg/cps | wt % (cps) |
| Fill | | |
| Dextromethorphan hydrobromide | 10.000 | 0.658 |
| Acetaminophen | 325.000 | 21.382 |
| Phenylephrine hydrochloride | 5.000 | 0.329 |
| Guaifenesin | 200.00 | 13.158 |
| Polyethylene Glycol | 540.000 | 35.526 |
| Povidone K12 | 40.000 | 2.632 |
| Shell | | |
| Gelatin | 237.419 | 15.620 |
| Liquid Sorbitol partially dehydrated | 63.312 | 4.165 |
| Glycerol IPEC | 63.312 | 4.165 |
| FD&C Red # 40 21CFR | 1319 | 0.087 |
| Candurin ® Silver Lustre | 2.638 | 0.174 |
| Purified water | 32.000 | 2.105 |
| Total | 1.520.000 | 100.000 |

Encapsulation.

During the encapsulation process, the suspension was stirred for 60 seconds every hour to maintain uniform dispersion. The suspension and outer shell mixture were introduced into an encapsulation machine to prepare the final soft gel capsules, with the machine parameters set as indicated in Table 8 below.

Post-Encapsulation Processing.

After encapsulation, the soft gel capsules were further processed according to standard methods in the art, as shown in FIG. 3, prior to packaging.

TABLE 8

| Encapsulation Parameters | |
|---|---|
| Parameter | Setting |
| Mean fill weight | Target: (1120.0 + 3.3%) mg/cps = 1157.0 mg/cps |
| Ribbon thickness | 0.035-0.039 in |
| Seam thickness | ≥0.012 in (for individual values) |

What is claimed is:

1. A soft gel capsule containing a suspension and an outer shell, wherein the suspension has a total volume of between about 0.50 mL and about 1.00 mL and the suspension consists of:
   between about 300 mg and about 400 mg acetaminophen;
   between about 5 mg and about 20 mg dextromethorphan HBr;
   between about 2.5 mg and about 10 mg phenylephrine HCl;
   optionally an antihistamine;
   between about 400 mg and about 500 mg polyethylene glycol;
   between about 25 mg and about 75 mg povidone; and
   less than or equal to 7.0 wt % adventitious water content.

2. The soft gel capsule of claim 1, wherein the suspension has a total volume of between about 0.60 mL and about 0.80 mL.

3. The soft gel capsule of claim 1, wherein the amount of acetaminophen in the suspension is about 325 mg.

4. The soft gel capsule of claim 1, wherein the amount of dextromethorphan HBr in the suspension is about 10 mg.

5. The soft gel capsule of claim 1, wherein the amount of phenylephrine HCl in the suspension is about 5 mg.

6. The soft gel capsule of claim 1, wherein the amount of acetaminophen in the suspension is about 325 mg, the amount of dextromethorphan HBr in the suspension is about 10 mg, and the amount of phenylephrine HCl in the suspension is about 5 mg.

7. The soft gel capsule of claim 1, wherein the antihistamine is present in an amount between about 1 and about 10 mg.

8. The soft gel capsule of claim 1, wherein the antihistamine is doxylamine succinate.

9. The soft gel capsule of claim 8, wherein the amount of doxylamine succinate in the suspension is about 6.25 mg.

10. The soft gel capsule of claim 1, wherein the antihistamine is chlorpheniramine maleate.

11. The soft gel capsule of claim 10, wherein the amount of chlorpheniramine maleate in the suspension is about 2 mg.

12. The soft gel capsule of claim 1, wherein the povidone has an average K value between 11 and 14.

13. The soft gel capsule of claim 1, wherein the outer shell comprises:
   gelatin;
   purified water;
   one or more plasticizers; and
   one or more colorants.

14. The soft gel capsule of claim 13, wherein the one or more colorants comprises a pearlescent pigment.

15. The soft gel capsule of claim 1, wherein the soft gel capsule has a water activity of between 0.40 and 0.50.

16. A soft gel capsule containing a suspension and an outer shell, wherein the suspension has a total volume of between about 0.80 mL and about 1.30 mL and the suspension consists of:

between about 300 mg and about 400 mg acetaminophen;
between about 5 mg and about 20 mg dextromethorphan HBr;
between about 2.5 mg and about 10 mg phenylephrine HCl;
between about 100 mg and about 300 mg guaifenesin;
between about 450 mg and about 550 mg polyethylene glycol;
between about 40 mg and about 60 mg povidone; and
less than or equal to 7.0 wt % adventitious water content.

17. The soft gel capsule of claim 16, wherein the amount of acetaminophen in the suspension is about 325 mg.

18. The soft gel capsule of claim 16, wherein the amount of dextromethorphan HBr in the suspension is about 10 mg.

19. The soft gel capsule of claim 16, wherein the amount of phenylephrine HCl in the suspension is about 5 mg.

20. The soft gel capsule of claim 16, wherein the amount of guaifenesin in the suspension is about 200 mg.

21. The soft gel capsule of claim 16, wherein the outer shell comprises:
gelatin;
purified water;
one or more plasticizers; and
one or more colorants.

22. The soft gel capsule of claim 21, wherein the one or more colorants comprises a pearlescent pigment.

23. The soft gel capsule of claim 16, wherein the soft gel capsule has a water activity of between 0.40 and 0.50.

24. A soft gel capsule containing a suspension and an outer shell, wherein the suspension has a total volume of between about 0.50 mL and about 1.00 mL and the suspension consists of:
between about 300 mg and about 400 mg acetaminophen;
between about 5 mg and about 20 mg dextromethorphan HBr; between about 2.5 mg and about 10 mg phenylephrine HCl;
optionally an antihistamine;
between about 400 mg and about 500 mg polyethylene glycol;
between about 25 mg and about 75 mg povidone; and
less than or equal to 7.0 wt % adventitious water content;
wherein the soft gel capsule has a total weight of less than about 1200 mg.

25. A soft gel capsule containing a suspension and an outer shell, wherein the suspension has a total volume of between about 0.80 mL and about 1.30 mL and the suspension consists of:
between about 300 mg and about 400 mg acetaminophen;
between about 5 mg and about 20 mg dextromethorphan HBr;
between about 2.5 mg and about 10 mg phenylephrine HCl;
between about 100 mg and about 300 mg guaifenesin;
between about 450 mg and about 550 mg polyethylene glycol;
between about 40 mg and about 60 mg povidone; and
less than or equal to 7.0 wt % adventitious water content,
wherein the soft gel capsule has a total weight of less than about 1600 mg.

26. A soft gel capsule, comprising an outer shell and a suspension, the suspension has a total volume of between about 0.80 mL and about 1.20 mL and wherein the suspension consists of:
at least 400 mg/mL acetaminophen;
at least 10.0 mg/mL dextromethorphan HBr, at least 5.0 mg/mL phenylephrine HCl;
between 400 mg/mL and 700 mg/mL polyethylene glycol;
between 30 mg/mL and 50 mg/mL povidone;
optionally an antihistamine; and
less than or equal to 7.0 wt % adventitious water content.

27. The soft gel capsule of claim 26, wherein the antihistamine is present.

28. The soft gel capsule of claim 27, wherein the antihistamine is doxylamine succinate and is in an amount in the suspension of at least 6.00 mg/mL.

29. The soft gel capsule of claim 27, wherein the antihistamine is chlorpheniramine maleate and is in an amount in the suspension of at least 1.00 mg/mL.

30. A soft gel capsule, comprising an outer shell and a suspension, the suspension has a total volume of between about 0.80 mL and about 1.20 mL and wherein the suspension consists of:
at least 250 mg/mL acetaminophen;
at least 7.00 mg/mL dextromethorphan HBr,
at least 2.00 mg/mL phenylephrine HCl;
at least 100 mg/mL guaifenesin;
between 400 mg/mL and 700 mg/mL polyethylene glycol;
between 30 mg/mL and 50 mg/mL povidone; and
less than or equal to 7.0 wt % adventitious water content.

\* \* \* \* \*